(12) United States Patent
Deshmukh et al.

(10) Patent No.: US 7,595,310 B2
(45) Date of Patent: *Sep. 29, 2009

(54) GLUCURONATE SALT OF A PIPERAZINE COMPOUND

(75) Inventors: Subodh S. Deshmukh, White Plains, NY (US); Kadum Ali, Congers, NY (US); Christopher R. Diorio, Campbell Hall, NY (US); Eric C. Ehrnsperger, Chestnut Ridge, NY (US); Mahdi B. Fawzi, Morristown, NJ (US); Syed Muzafar Shah, East Hanover, NJ (US); Mahmoud Mirmehrabi, Laval (CA)

(73) Assignee: Solvay Pharmaceuticals, B.V., Weesp (NL)

( * ) Notice: Subject to any disclaimer, the term of this patent is extended or adjusted under 35 U.S.C. 154(b) by 137 days.

This patent is subject to a terminal disclaimer.

(21) Appl. No.: 11/519,756

(22) Filed: Sep. 12, 2006

(65) Prior Publication Data

US 2007/0254876 A1    Nov. 1, 2007

Related U.S. Application Data

(60) Provisional application No. 60/716,167, filed on Sep. 12, 2005.

(51) Int. Cl.
*A01N 43/00* (2006.01)
*A61K 31/33* (2006.01)

(52) U.S. Cl. .................... 514/183; 514/192; 514/224.2; 514/228.8; 514/230.5

(58) Field of Classification Search .................. None
See application file for complete search history.

(56) References Cited

U.S. PATENT DOCUMENTS

| | | | |
|---|---|---|---|
| 4,438,119 A | 3/1984 | Allen et al. | |
| 4,687,772 A | 8/1987 | Alderdice | |
| 4,771,053 A | 9/1988 | Cott et al. | |
| 5,162,375 A | 11/1992 | Nicholson et al. | |
| 5,824,680 A | 10/1998 | Turner et al. | |
| 6,958,396 B2 * | 10/2005 | Bakker ..................... | 544/105 |
| 2005/0215526 A1 | 9/2005 | Hulme et al. | |
| 2007/0060580 A1 | 3/2007 | Deshmukh et al. | |

FOREIGN PATENT DOCUMENTS

| | | |
|---|---|---|
| WO | WO 93/04681 A1 | 3/1993 |
| WO | WO 00/16777 A1 | 3/2000 |
| WO | WO 00/43378 A1 | 7/2000 |
| WO | WO 01/14330 A2 | 3/2001 |
| WO | WO 01/52855 A2 | 7/2001 |
| WO | WO 02/066473 A1 | 8/2002 |
| WO | WO 2005/061493 A2 | 7/2005 |
| WO | WO 2007/33191 A1 | 3/2007 |
| WO | WO 2007/033192 A1 | 3/2007 |
| WO | WO 2007/033193 A2 | 3/2007 |
| WO | WO 2007/033193 A3 | 3/2007 |

OTHER PUBLICATIONS

Lander et al. Nature 409:860 (2001).
Van Der Poel et al. Psychopharmacology, 97:147 (1989).
Van Der Heyden and Bradford. Behav. Brain Res. 31:61 (1988).
Sedvall et al. The Lancet, 346:743-749, (1995).
Hietala. The Lancet, 346:1130-1131 (1995).
Kemppainen et al. Eur J Neurosci., 18:149-154 (2003).
Kleven et al. European Journal of Pharmacology, 281:219-228 (1995).
Leone et al. Neuro Report, 9:2605-2608 (1998).
De Vry et al. European Journal of Pharmacology, 357:1-8 (1998).
Wolff et al. European Journal of Pharmacology, 340:217-220 (1997).
Alfieri et al. British Journal of Cancer, 72:1013-1015 (1995).
Wolff et al., Pharmacology Biochemistry and Behavior, 52:571-575 (1995).
Lucot. European Journal of Pharmacology, 253:53-60 (1997).
Rasmussen et al. Annual Reports in Medicinal Chemistry, 30:1-9 (1995).
Millan, Journal of Pharmacology and Experimental Therapeutics, 295:853-861 (2000).
Ungerstedt. Acta Physiol. Scand. 82: (suppl. 367) 69 (1971).
Hagger et al. Biol. Psychiatry, 34:702 (1993).
Sharma et al. J. Clin. Psychopharmacol., 18:128 (1998).
Lee et al. J. Clin. Psychiatry, 55:82 (1994).
Fujii, et al. J. Neuropsychiatry Clin. Neurosci., 9:240 (1997).
Mason et al. Eur. J. Pharmacol., 221:397 (1992).
Newman-Tancredi et al. Neuropharmacology, 35:119, (1996).
Sumiyoshi et al. J. Clin. Pharmacol., 20:386 (2000).
Carli et al. Eur. J. Neurosci., 10:221 (1998).
Meneses et al. Neurobiol. Learn. Mem., 71:207 (1999).
Glennon et al. Neuroscience and Behavioral Reviews, 14:3547 (1990).
Masson et al. Pharm. Rev. 51:439 (1999).
International Search Report for PCT/US2006/035517, Date of mailing: Feb. 7, 2007.
Berge et al., "Pharmaceutical Salts," Journal of Pharmaceutical Sciences, vol. 66, No. 1, Jan. 1977 (Jan. 1977), pp. 1-19.

(Continued)

*Primary Examiner*—Patrick T Lewis
(74) *Attorney, Agent, or Firm*—Finnegan, Henderson, Farabow, Garrett & Dunner, L.L.P.

(57) ABSTRACT

The present invention provides a salt form, and compositions thereof, useful as a modulator of one or more GPCRs and which exhibits desirable characteristics for the same. The present invention also provides methods for preparing said salt form.

25 Claims, 22 Drawing Sheets

OTHER PUBLICATIONS

Das and Khan, "Increased arachidonic acid induced platelet chemiluminescence indicates cyclooxygenase overactivity in schizophrenic subjects," Prostaglandins Leukot Essent Fatty Acids 58:165-168 (1998).

International Search Report for PCT/US2006/035519, Dated Dec. 7, 2006.

Copending U.S. Appl. No. 11/519,738, filed Sep. 12, 2006, Published Mar. 15, 2007, US-2007-0060580-A1.

Copending U.S. Appl. No. 11/519,763, filed Sep. 12, 2006, Published Mar. 15, 2007, US-2007-0059366-A1.

Office Action mailed Feb. 2, 2009, in co-pending U.S. Appl. No. 11/519,763, Examiner Samala.

Office Action mailed Apr. 1, 2009, in co-pending U.S. Appl. No. 11/519,738, Examiner K. Habte.

Office Action mailed Dec. 15, 2008, in co-pending U.S. Appl. No. 11/519,738, Examiner K. Habte.

* cited by examiner

Peak Search Report (15 Peaks, Max P/N = 23.1)
[98 Glucuronate.RAW] Glucuronic 98-
PEAK: 35-pts/Parabolic Filter, Threshold=9.0, Cutoff=0.1%, BG=3/1.0, Peak-Top=Summit

| 2-Theta | d(Å) | BG | Height | I% | Area | I% | FWHM |
|---|---|---|---|---|---|---|---|
| 3.9 | 22.6394 | 251 | 831 | 30 | 42596 | 53.9 | 0.871 |
| 4.321 | 20.4344 | 244 | 574 | 20.7 | 21874 | 27.7 | 0.648 |
| 7.599 | 11.6238 | 302 | 153 | 5.5 | 2505 | 3.2 | 0.262 |
| 11.12 | 7.9503 | 464 | 313 | 11.3 | 7124 | 9 | 0.387 |
| 12.238 | 7.2262 | 509 | 356 | 12.8 | 7165 | 9.1 | 0.342 |
| 14.515 | 6.0973 | 744 | 140 | 5 | 406 | 0.5 | 0.046 |
| 15.24 | 5.8089 | 860 | 603 | 21.7 | 20962 | 26.5 | 0.591 |
| 16.341 | 5.4201 | 1009 | 317 | 11.4 | 4219 | 5.3 | 0.213 |
| 17.501 | 5.0634 | 834 | 2773 | 100 | 79011 | 100 | 0.484 |
| 19.319 | 4.5907 | 783 | 317 | 11.4 | 8373 | 10.6 | 0.449 |
| 19.979 | 4.4404 | 774 | 483 | 17.4 | 16442 | 20.8 | 0.579 |
| 21.399 | 4.1489 | 708 | 286 | 10.3 | 4620 | 5.8 | 0.275 |
| 22.48 | 3.9518 | 771 | 1127 | 40.6 | 37415 | 47.4 | 0.564 |
| 24.963 | 3.5612 | 685 | 106 | 3.8 | 1057 | 1.3 | 0.16 |
| 25.94 | 3.4319 | 681 | 571 | 20.6 | 23950 | 30.3 | 0.713 |

FIG. 1b

GLUCURONATE SALT OF A PIPERAZINE COMPOUND

CROSS-REFERENCE TO RELATED APPLICATIONS

The present invention claims priority to U.S. provisional patent application Ser. No. 60/716,167, filed Sep. 12, 2005, the entirety of which is hereby incorporated herein by reference.

FIELD OF THE INVENTION

The present invention provides salt forms, and compositions thereof, useful as modulators of one or more GPCRs.

BACKGROUND OF THE INVENTION

The G-protein coupled receptor (GPCR) family is the largest known gene family representing greater than 1% of the human genome, and encompassing a wide range of biological functions (including various autocrine, paracrine and endocrine processes). The GPCR superfamily is also the most exploited gene family by the pharmaceutical industry for the development of therapeutic compounds. GPCRs have been categorized into rhodopsin-like GPCRs, the secretin-like GPCRs, the cAMP receptors, the fungal mating pheromone receptors, and the metabotropic glutamate receptor family. The rhodopsin-like GPCRs themselves represent a widespread protein family that includes hormone, neurotransmitter and light receptors, all of which transduce extracellular signals through interaction with guanine nucleotide-binding (G) proteins. Although their activating ligands vary widely in structure and character, the amino acid sequences of rhodopsin-like GPCRs are very similar and are believed to adopt a common structural framework comprising 7 transmembrane (TM) spanning a-helices and are coupled to G-proteins within the cell which dissociate from the receptor on agonist binding and initiate or inhibit secondary messenger signalling mechanisms. See: Lander et al. Nature 409:860 (2001); Basic and clinical pharmacology, $8^{th}$ Ed., Katzung. USA: The McGraw Hill Companies, Inc. (2001).

The rhodopsin-like GPCR family includes several classes of receptors which are variously distributed throughout the central nervous system (CNS) and many peripheral sites and have been implicated in a variety of CNS and neuropsychiatric conditions. Included among these receptors are dopamine ("D") receptors, and 6 of 7 main subtypes of serotonin (5-hydroxytryptamine, "5HT") receptors (5HT$_{1,2}$ and $_{4-7}$ receptor subtypes are GPCRs while the 5HT$_3$ receptor subtypes are ligand-gated Na$^+$/K$^+$ ion channel).

Dopamine neurons in the vertebrate central nervous system are involved in the initiation and execution of movement, the maintenance of emotional stability, and the regulation of pituitary function. Dopamine binding to the extracellular binding groove of D receptors activates G-proteins—the D$_1$ and D$_5$ receptor subtypes ("D$_1$-like") are linked to stimulatory G-proteins, whereas receptor subtypes 2-4 ("D$_2$-like") are linked to inhibitory G-proteins. D$_2$-like receptors are found through out the brain and in smooth muscle and presynaptic nerve terminals and have an inhibitory effect on neurotransmission when bound by an agonist. Specifically, D$_2$ receptors are abundant and widespread in the striatum, limbic system, thalamus, hypothalamus, and pituitary gland). Antagonist binding to D$_2$ receptors inhibits agonist binding and therefore prevents the inhibition of down-stream signalling mechanisms. Antagonists of D$_2$ receptors are used in the treatment of psychoses (e.g., schizophrenia, mania, psychotic depression, and bipolar disorder), and show utility for short-term sedation in aggression or agitation (e.g., amisulpride, clozapine, haloperidol, nemonapride, pimozide, remoxipride, spiperone, sulpiride) and may be useful for treating drug addicion, while agonists of D$_2$ receptors are used in the treatment of Parkinson's disease and to suppress prolactin secretion arising from tumours of the pituitary gland (e.g., apomorphine, bromocriptine, dihydroergotamine, piribedil, quinpirole), and to treat restless legs syndrome (RLS; e.g., pramipexole, ropinirole). See: Basic and clinical pharmacology, $8^{th}$ Ed., Katzung. USA: The McGraw Hill Companies, Inc. (2001); Pharmacology, $4^{th}$ Ed., Rang et al. Edinburgh, UK: Harcourt Publishers Ltd. (2001); Sedvall et al. The Lancet, 346:743-749, (1995); Hietala. The Lancet, 346:1130-1131 (1995); Kemppainen et al. Eur J Neurosci., 18:149-154 (2003)

5-Hydroxytryptamine is ubiquitous in plants and animals. It is an important neurotransmitter and local hormone in the CNS and intestine, and is implicated in a vast array of physiological and pathophysiological pathways. 5-Hydroxytryptamine binding to the extracellular binding groove of 5HT receptors activates G-proteins—the 5HT$_1$ receptor subtypes are known to be linked to inhibitory G-proteins, whereas subtypes 2, 4, 6 and 7 are known to be linked to stimulatory G-proteins. Of these, 5HT$_1$ receptor subtypes (at least 5 are known) are known to occur primarily in the brain and cerebral blood vessels where they mediate neural inhibition and vasoconstriction. Specific agonists at 5HT$_1$ receptors are used in migraine therapy (e.g., sumatriptan) and in the treatment of stress/anxiety (e.g., buspirone), while antagonists have been recommended in the treatment of psychoses (e.g., spiperone, methiothepin). Additionally, regulation of the 5HT$_1$ receptor subtypes have been implicated in drug addiction, Alzheimer's disease, Parkinson's disease, depression, emesis, and eating disorders. 5HT$_2$ receptor subtypes (at least 3 are known) are found throughout the CNS and at many peripheral sites where they produce excitatory neuronal and smooth muscle effects. 5HT$_2$ receptor antagonists are employed in migraine therapy (e.g., methisergide) and have shown potential in the treatment of scleroderma and Raynaud's phenomenon (e.g., ketanserin). 5HT$_3$ receptors are known to occur mainly in the peripheral nervous system and antagonists are employed as anti-emetics (e.g., ondansetron, tropisetron). 5HT$_4$ receptors are found in the brain, as well as the heart, bladder and gastrointestinal (GI) tract. Within the GI tract they produce neuronal excitation and mediate the effect of 5HT in stimulating peristalsis. Specific 5HT$_4$ receptor antagonists are used for treating GI disorders (e.g., metoclopramide). 5HT receptor subtypes 5 (at least 5 are known), 6, and 7 are also found throughout the CNS and may be potential targets for small-molecule drugs. In particular, the 5HT$_7$ receptor subtype has been implicated in depression, psychoses, Parkinson's disease, Alzheimer's disease, Huntington's disease, migraine, stress/anxiety, eating disorders, and emesis. See: Basic and clinical pharmacology, $8^{th}$ Ed., Katzung. USA: The McGraw Hill Companies, Inc. (2001); Pharmacology, $4^{th}$ Ed., Rang et al. Edinburgh, UK: Harcourt Publishers Ltd. (2001); Kleven et al. European Journal of Pharmacology, 281:219-228 (1995); U.S. Pat. No. 5,162,375; Leone et al. Neuro Report, 9:2605-2608(1998); U.S. Pat. No. 4,771,053; WO 01/52855; De Vry et al. European Journal of Pharmacology, 357:1-8 (1998); Wolff et al. European Journal of Pharmacology, 340:217-220 (1997); Alfieri et al. British Journal of Cancer, 72:1013-1015 (1995); Wolff et al., Pharmacology Biochemistry and Behavior, 52:571-575 (1995); Lucot. European Journal of Pharmacology, 253:53-60 (1997); U.S. Pat. Nos. 5,824,680; 4,687,772; Rasmussen et al. Annual Reports in Medicinal Chemistry, 30:1-9 (1995); WO 00/16777; U.S. Pat. No. 4,438,119; Millan, Journal of Pharmacology and Experimental Therapeutics, 295:853-861 (2000); WO 93/04681; Miyamoto, et al. Current Opinion in CPNS Investigational Drugs, 2:25 (2000); Hagger, et al. Biol. Psychiatry, 34:702 (1993); Sharma et al. J. Clin. Psychopharmacol., 18:128 (1998); Lee et al. J. Clin. Psychiatry, 55:82 (1994); Fujii, et al. J. Neuropsychiatry Clin. Neurosci., 9:240 (1997); Mason et al. Eur. J. Pharmacol., 221:397 (1992); Newman-Tancredi et al. Neuropharmacology, 35:119, (1996); Sumiyoshi et al. J. Clin. Pharmacol., 20:386 (2000); Carli et al. Eur. J. Neurosci., 10:221 (1998); Meneses et al. Neurobiol. Learn. Mem., 71:207 (1999); and Glennon et al. Neuroscience and Behavioral Reviews, 14:3547 (1990).

The action of 5HT at synapses is terminated by its $Na^+/K^+$-mediated reuptake across the pre-synaptic membrane. 5HT-reuptake inhibitors are employed in the treatment of depression, stress/anxiety, panic disorder, obsessive compulsive disorder, eating disorders, and social phobias, (e.g., citalopram, clomipramine, fluoxetine, fluvoxamine, indatraline, zimelidine) and may be useful in the treatment of migraine, psychoses, Alzheimer's disease, Parkinson's disease, Huntington's disease, drug addiction, eating disorders, scleroderma and Raynauds phenomenon, GI tract disorders related to the regulation of peristalsis, and/or emesis. See: Basic and clinical pharmacology, $8^{th}$ Ed., Katzung. USA: The McGraw Hill Companies, Inc. (2001); Pharmacology, $4^{th}$ Ed., Rang et al. Edinburgh, UK: Harcourt Publishers Ltd. (2001); Masson et al. Pharm. Rev. 51:439 (1999); and additionally, the references in the preceding paragraphs.

Accordingly, it would be desirable to provide compounds which modulate GPCRs in a form suitable for administration to a patient in need of treatment for any of the above-mentioned disorders. In particular, it would be desirable for such compounds to exhibit additional characteristics such as good solubility, stability and ease of formulation, etc.

SUMMARY OF THE INVENTION

It has now been found that the novel salt form of the present invention, and compositions thereof, is useful as a modulator of one or more GPCRs and exhibits desirable characteristics for the same. In general, this salt form, and pharmaceutically acceptable compositions thereof, is useful for treating or lessening the severity of a variety of diseases or disorders including, but not limited to, Parkinson's disease, psychoses (e.g., schizophrenia, mania, psychotic depression, and bipolar disorder), depression, stress/anxiety, Alzheimer's disease, Huntington's disease, panic disorder, obsessive compulsive disorder, eating disorders, drug addiction, social phobias, aggression or agitation, migraine, scleroderma and Raynaud's phenomenon, emesis, GI tract disorders related to the regulation of peristalsis, RLS, and prolactin secretion arising from tumours of the pituitary gland.

DETAILED DESCRIPTION OF THE INVENTION

Figure 1A:
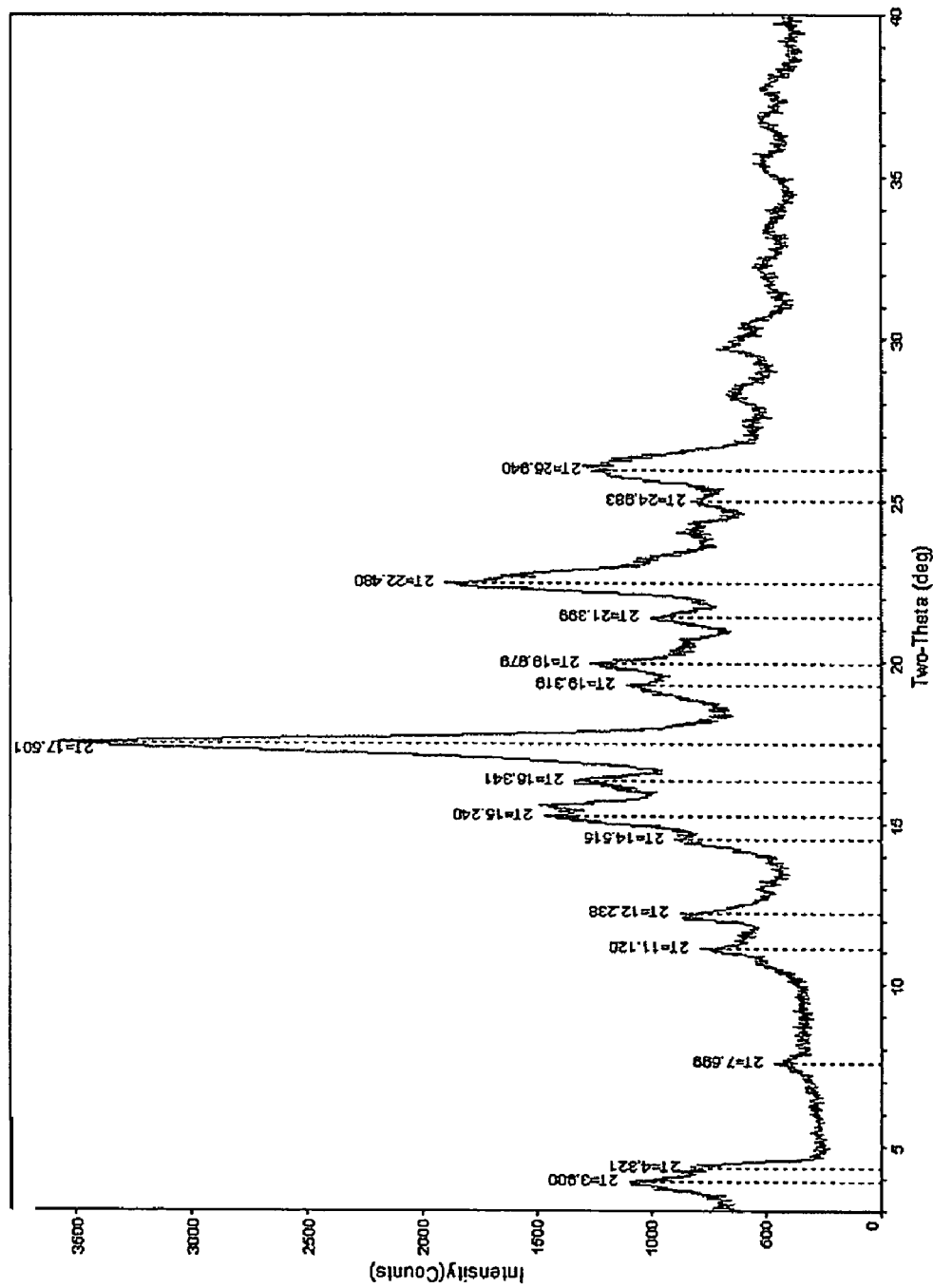
FIG. 1 depicts the X-ray powder diffraction pattern for Form I of compound 2.

General Description of Certain Aspects of the Invention

International patent application number PCT/EP/00/08190 (International publication number WO 01/14330) describes various indole-containing piperazine derivatives, including compound 1 (8-{4-[3-(5-fluoro-1H-indol-3-yl)-propyl]-piperazin-1-yl}-2-methyl-4H-benzo[1,4]oxazin-3-one, shown), which exhibit antagonistic activity at $D_2$ receptors and inhibitory activity against 5HT reuptake in therapeutic models.

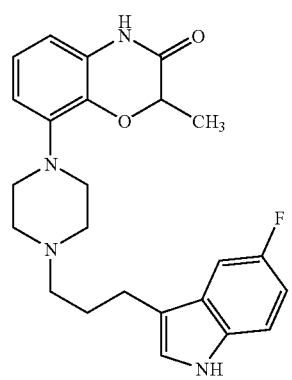

1

Additionally, compound 1 is active in therapeutic models which are sensitive to clinically relevant antipsychotics, antidepressants, and anxiolytics, as well as Parkinson's disease. Accordingly, compound 1 is useful for treating Parkinson's disease, psychoses (e.g., schizophrenia, mania, psychotic depression, and bipolar disorder), depression, stress/anxiety, panic disorder, Alzheimer's disease, obsessive compulsive disorder, eating disorders, drug addiction, social phobias, aggression or agitation, migraine, scleroderma and Raynaud's phenomenon, emesis, GI tract disorders related to the regulation of peristalsis, RLS, and to suppress prolactin secretion arising from tumours of the pituitary gland. Furthermore, compound 1 has a low propensity to induce catalepsy in rodents and is therefore less likely to induce extrapyramidal side effects than existing antipsychotics. See: WO 01/14330; van der Heyden and Bradford. Behav. Brain Res. 31:61 (1988); van der Poel et al. Psychopharmacology, 97:147 (1989); and Ungerstedt. Acta Physiol. Scand. 82: (suppl. 367) 69 (1971).

It would be desirable to provide a salt form of compound 1 that, as compared to compound 1, imparts characteristics such as improved aqueous solubility, stability and ease of formulation. In particular, improved aqueous solubility would be advantageous by providing an improved dissolution in the GI tract, thus improving absorption and bioavailability. Improved bioavailablility would allow for a lower dose, which in turn could produce fewer adverse GI effects such as nausea or emesis. Lower dosage could also allow for the development of a smaller dosage form (e.g., tablet, capsule) which would be beneficial from the drug processing standpoint and would improve patient compliance (i.e., patients prefer taking smaller tablets or capsules). Additionally, a once daily dosage form would also improve patient compliance over multiple dosing, which is an important consideration for the relevant patient population such as individuals suffering from schizophrenia or other psychoses. Accordingly, the present invention provides the glucuronate salt of compound 1 in a form suitable for extended release formulation, which form would have the added benefits of reducing adverse upper GI effects such as nausea or emesis by limiting the amount of drug release there and by-passing the receptors in the upper GI that are responsible for said effects.

According to one embodiment, the present invention provides a glucuronate salt of compound 1, represented by compound 2:

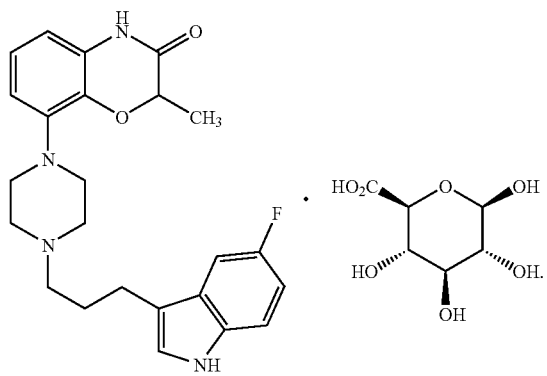

2

It will be appreciated by one of ordinary skill in the art that the glucuronic acid and compound 1 are ionically bonded to form compound 2. It is contemplated that compound 2 can exist in a variety of physical forms. For example, compound 2 can be in solution, suspension, or in solid form. In certain embodiments, compound 2 is in solid form. When compound 2 is in solid form, said compound may be amorphous, crystalline, or a mixture thereof. Exemplary solid forms are described in more detail below.

As used herein, notwithstanding the structure of compound 2 depicted above, the phrase "glucuronic acid salt," and related terms, refers to the D-glucuronic acid salt, the L-glucuronic acid salt, the DL-glucuronic acid salt, or mixtures thereof. In certain embodiments, compound 2 is the D-glucuronic acid salt. In other embodiments, compound 2 is the D-glucuronic acid salt which is substantially free of the L-glucuronic acid salt, wherein "substantially free" means that the compound contains no significant amount of L-glucuronic acid salt. In certain embodiments, at least about 95% by weight of compound 2 is present as the D-glucuronic acid salt. In still other embodiments of the invention, at least about 99% by weight of compound 2 is present as the D-glucuronic acid salt.

One of ordinary skill in the art will recognize that glucuronic acid can exist in the cyclic form, as depicted above, or in a ring-opened form. Accordingly, the present invention contemplates that the glucuronate salt, compound 2, includes both the cyclic glucuronic acid salt and the ring-opened glucuronic acid salt forms.

In other embodiments, the present invention provides compound 2 substantially free of impurities. As used herein, the term "substantially free of impurities" means that the compound contains no significant amount of extraneous matter. Such extraneous matter may include excess glucuronic acid, excess compound 1, residual solvents, or any other impurities that may result from the preparation of, and/or isolation of, compound 2. In certain embodiments, at least about 95% by weight of compound 2 is present. In still other embodiments of the invention, at least about 99% by weight of compound 2 is present.

According to one embodiment, compound 2 is present in an amount of at least about 97, 97.5, 98.0, 98.5, 99, 99.5, 99.8 weight percent where the percentages are based on the total weight of the composition. According to another embodiment, compound 2 contains no more than about 2.0 area percent HPLC of total organic impurities and, in certain embodiments, no more than about 1.5 area percent HPLC total organic impurities relative to the total area of the HPLC chromatogram. In other embodiments, compound 2 contains no more than about 0.6 area percent HPLC of any single impurity, and, in certain embodiments, no more than about 0.5 area percent HPLC of any single impurity, relative to the total area of the HPLC chromatogram.

The structure depicted for compound 2 is also meant to include all isomeric (e.g., enantiomeric or conformational) forms of the structure. For example, both the R and the S configurations at the stereogenic carbon are included in this invention. Therefore, single stereochemical isomers as well as enantiomeric and conformational mixtures of the present compound are within the scope of the invention. Furthermore, all tautomeric forms of compound 2 are within the scope of the present invention. Additionally, structures depicted here are also meant to include compounds that differ only in the presence of one or more isotopically enriched atoms. For example, compounds having the present structure except for the replacement of hydrogen by deuterium or tritium, or the replacement of a carbon by a $^{13}C$- or $^{14}C$-enriched carbon are within the scope of this invention.

Solid Forms of Compound 2:

It has been found that compound 2 can exist in a variety of solid forms. Such forms include neat crystal forms, also known as polymorphs, solvates, hydrates, and amorphous. All such forms are contemplated by the present invention. In certain embodiments, the present invention provides compound 2 as a mixture of one or more solid forms selected from polymorphs, solvates, hydrates, and amorphous compound 2.

As used herein, the term "polymorph" refers to the different crystal structures (of unsolvated forms) in which a compound can crystallize. As used herein, the term "solvate" refers to a crystal form with either a stoichiometric or non-stoichiometric amount of solvent is incorporated into the crystal structure. Similarly, the term "hydrate" refers to a crystal form with either a stoichiometric or non-stoichiometric amount of water is incorporated into the crystal structure.

In certain embodiments, compound 2 is a crystalline solid. In other embodiments, compound 2 is a crystalline solid substantially free of amorphous compound 2. As used herein, the term "substantially free of amorphous compound 2" means that the compound contains no significant amount of amorphous compound 2. In certain embodiments, at least about 95% by weight of crystalline compound 2 is present. In still other embodiments of the invention, at least about 99% by weight of crystalline compound 2 is present.

In certain embodiments, compound 2 is a neat crystal form and thus does not have any water or solvent incorporated into the crystal structure. It has been found that compound 2 can exist in at least two distinct neat crystal forms, or polymorphs. Two such polymorphic forms are referred to herein as Form I and Form II.

Figure 5:
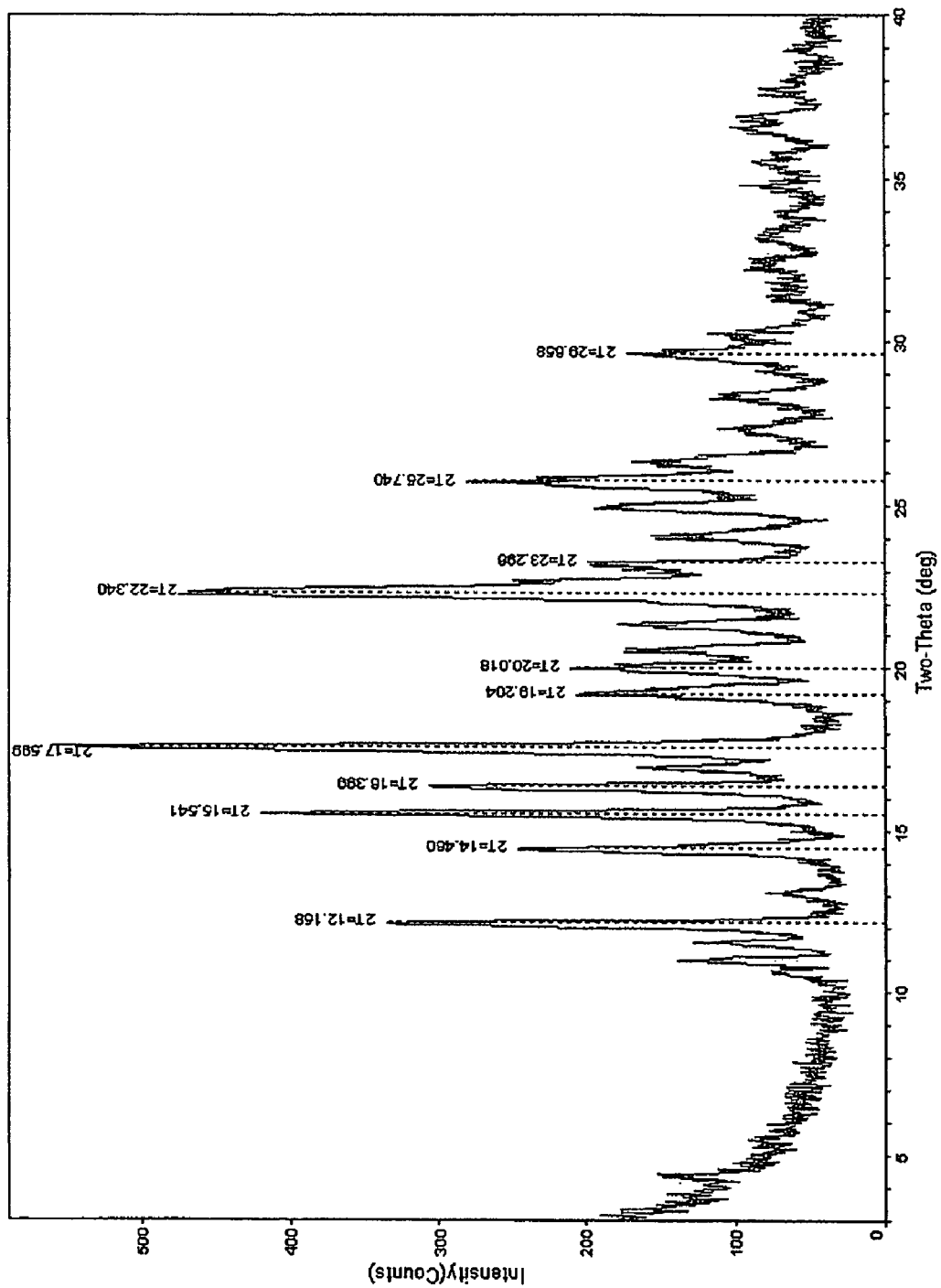
FIG. 5 depicts the X-ray powder diffraction pattern for Form I of compound 2.

In certain embodiments, the present invention provides Form I of compound 2. According to one aspect, Form I of compound 2 has a powder X-ray diffraction pattern substantially similar to that depicted in FIG. 1 or 5. According to another embodiment, Form I of compound 2 is characterized in that it has one or more peaks in its powder X-ray diffraction pattern selected from those at about 17.5, 22.5, 19.9, 3.9, and 12.2 degrees 2-theta. As used herein, the term "about", when used in reference to a degree 2-theta value refers to the stated value ±0.1 degree 2-theta. Methods for preparing Form I of compound 2 are described infra.

In other embodiments, the present invention provides Form II of compound 2. According to one embodiment, Form II of compound 2 has a characteristic peak in its powder X-ray diffraction pattern selected from those at about 18.7 degrees 2-theta. Methods for preparing Form II of compound 2 are described infra.

Figure 7:
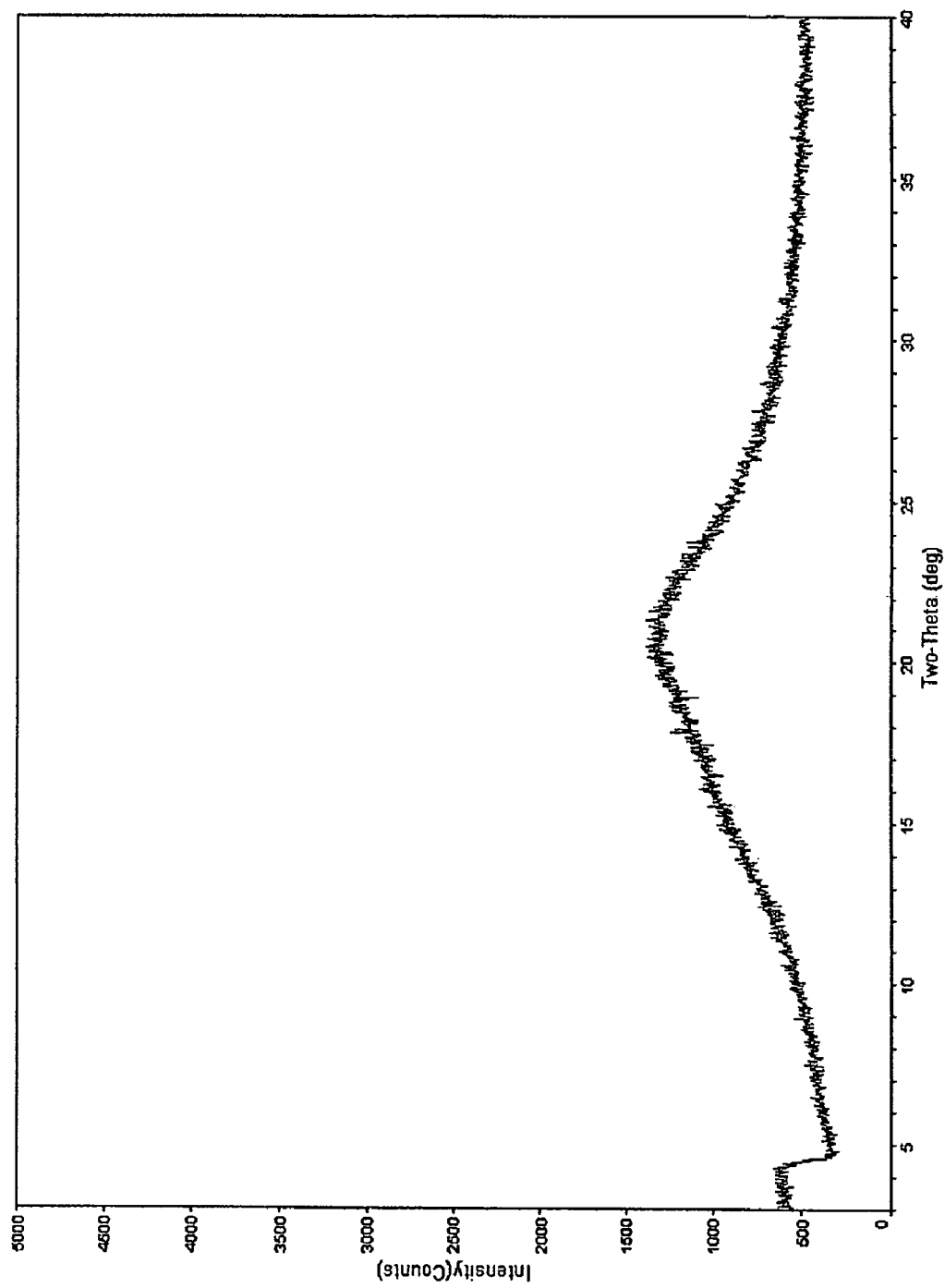
FIG. 7 depicts the X-ray powder diffraction pattern for amorphous compound 2.

According to another embodiment, the present invention provides compound 2 as an amorphous solid. The powder X-ray diffraction pattern of amorphous compound 2 is depicted in FIG. 7. Amorphous solids are well known to one of ordinary skill in the art and are typically prepared by such methods as lyophilization, melting, and precipitation from supercritical fluid, among others. Other methods of preparing amorphous compound 2 are described herein infra.

It has been found that compound 2 can exist in at least two hydrate forms. The two hydrate forms are referred to herein as Hydrate I and Hydrate II.

Figure 9:
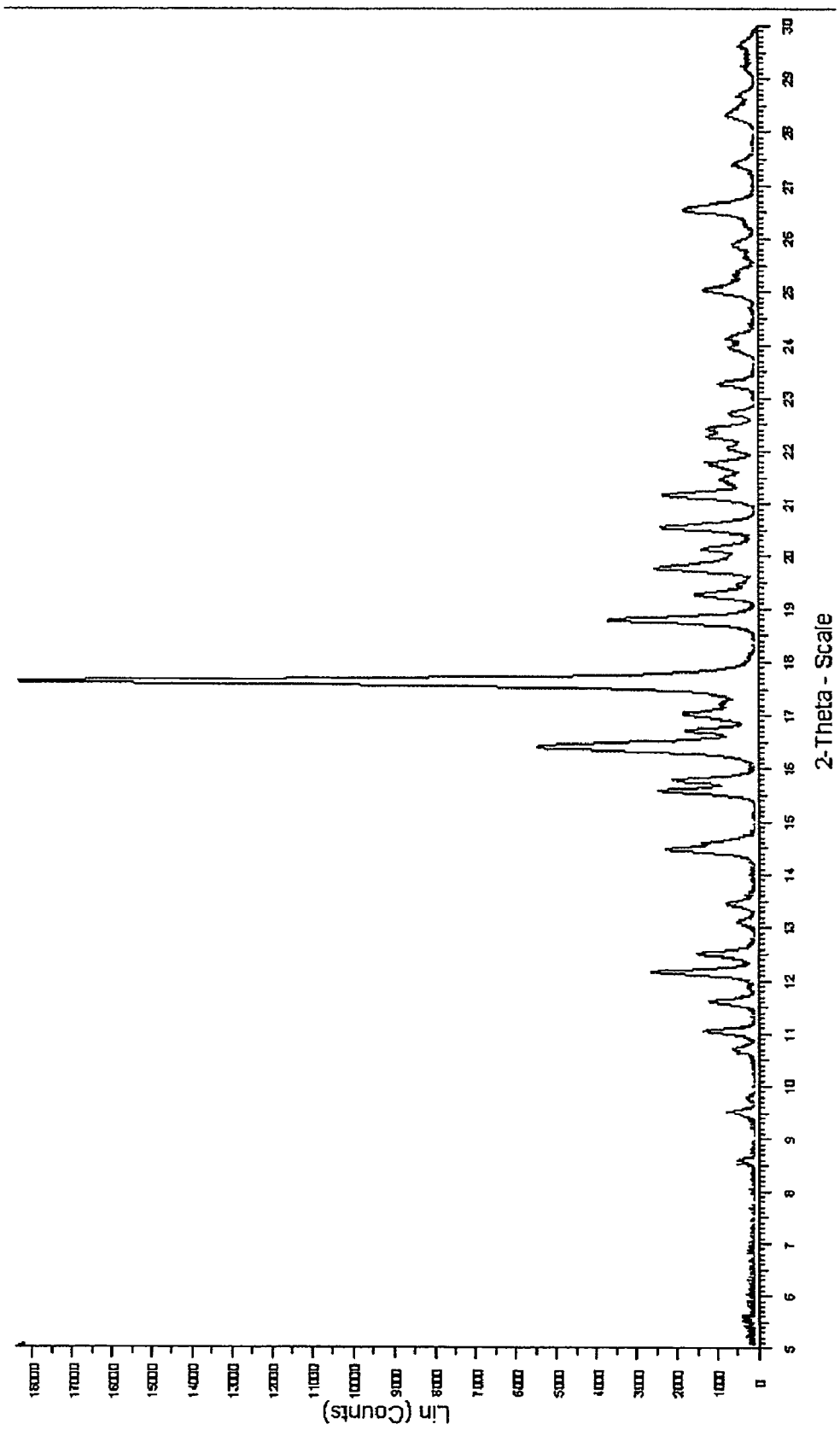
FIG. 9 depicts the X-ray powder diffraction pattern for Hydrate I of compound 2.

In certain embodiments, the present invention provides Hydrate I of compound 2. According to one embodiment, Hydrate I is characterized in that it has one or more peaks in its powder X-ray diffraction pattern selected from those at about 9.49, 16.40, and 17.61 degrees 2-theta. According to one aspect, Hydrate I of compound 2 has a powder X-ray diffraction pattern substantially similar to that depicted in FIG. 9. Methods for preparing Hydrate I of compound 2 are described infra.

Table 1 below sets out the X-ray diffraction peaks observed for Hydrate I of compound 2 wherein each value is in degrees 2-theta.

TABLE 1

Observed X-ray diffraction peaks for Hydrate I of compound 2

| Angle 2-Theta ° | d value Angstrom | Intensity % |
|---|---|---|
| 9.49 | 9.31 | 3.90 |
| 10.68 | 8.28 | 3.10 |
| 11.02 | 8.02 | 7.00 |
| 11.58 | 7.64 | 6.40 |
| 12.14 | 7.29 | 14.00 |
| 12.49 | 7.08 | 8.00 |
| 13.43 | 6.59 | 4.00 |
| 14.46 | 6.12 | 12.10 |
| 14.57 | 6.07 | 7.30 |
| 15.57 | 5.69 | 13.20 |
| 15.77 | 5.61 | 11.10 |
| 16.40 | 5.40 | 29.50 |
| 16.71 | 5.30 | 9.50 |
| 17.02 | 5.21 | 9.80 |
| 17.61 | 5.03 | 100.00 |
| 18.79 | 4.72 | 20.00 |
| 19.27 | 4.60 | 8.10 |
| 19.76 | 4.49 | 13.40 |
| 20.14 | 4.41 | 7.30 |
| 20.55 | 4.32 | 12.80 |
| 21.16 | 4.20 | 12.60 |
| 21.46 | 4.14 | 4.80 |
| 21.76 | 4.08 | 6.20 |
| 22.05 | 4.03 | 3.70 |
| 22.27 | 3.99 | 6.70 |
| 22.41 | 3.96 | 6.60 |
| 22.70 | 3.91 | 3.50 |
| 23.26 | 3.82 | 5.10 |
| 23.94 | 3.71 | 3.50 |
| 24.13 | 3.68 | 3.70 |
| 25.03 | 3.55 | 7.10 |
| 25.89 | 3.44 | 3.20 |
| 26.55 | 3.35 | 9.80 |
| 27.41 | 3.25 | 3.10 |
| 28.33 | 3.15 | 4.10 |

Figure 11:
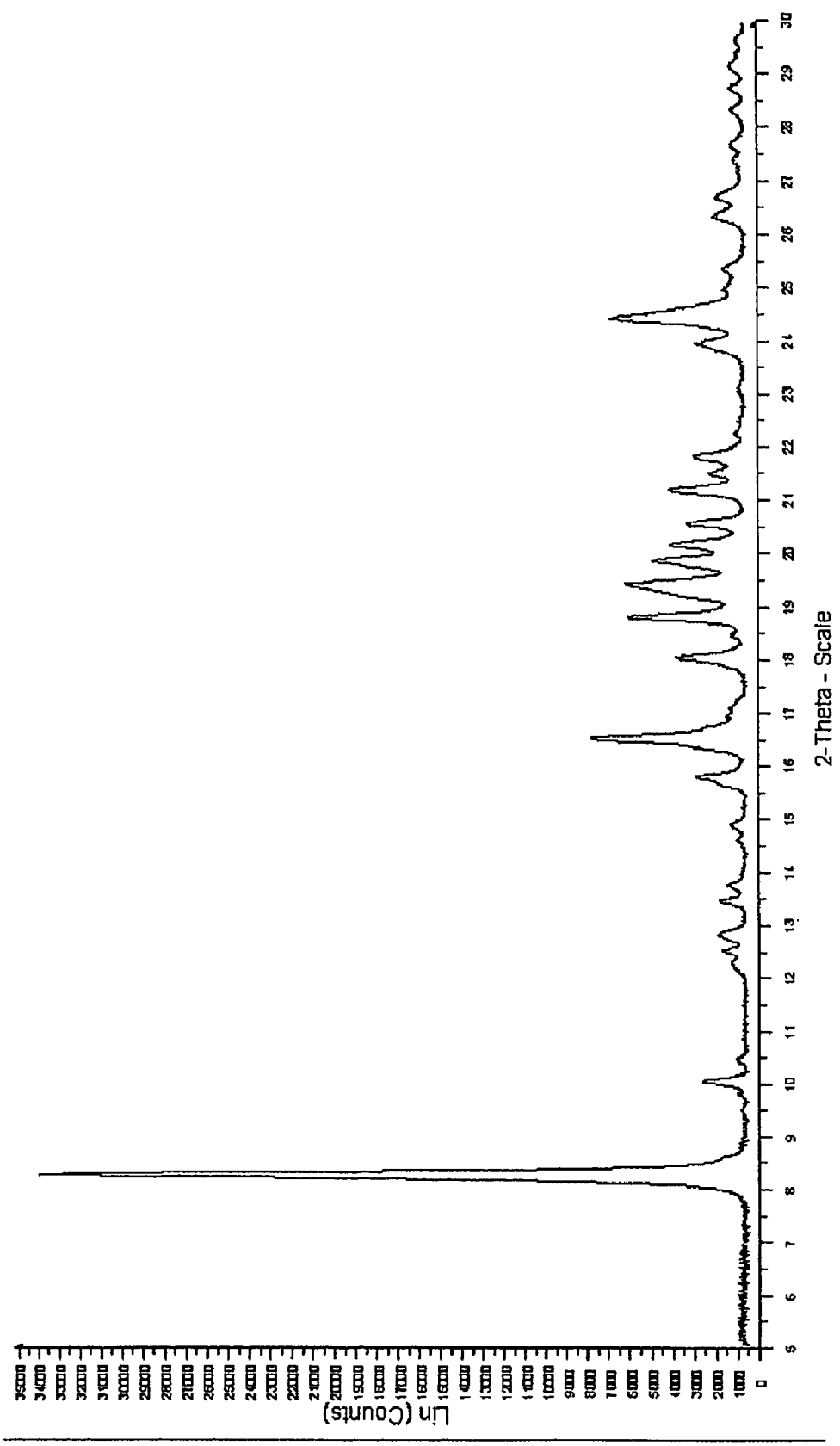
FIG. 11 depicts the X-ray powder diffraction pattern for Hydrate II of compound 2.

In certain embodiments, the present invention provides Hydrate II of compound 2. According to one embodiment, Hydrate II is characterized in that it has one or more peaks in its powder X-ray diffraction pattern selected from those at about 8.252, 10.015, 16.511, and 24.42 degrees 2-theta. According to one aspect, Hydrate II of compound 2 has a powder X-ray diffraction pattern substantially similar to that depicted in FIG. 11. Methods for preparing Hydrate II of compound 2 are described infra.

Table 2 below sets out the X-ray diffraction peaks observed for Hydrate II of compound 2 wherein each value is in degrees 2-theta.

TABLE 2

Observed X-ray diffraction peaks for Hydrate II of compound 2

| Angle 2-Theta ° | d value Angstrom | Intensity % |
|---|---|---|
| 8.252 | 10.70662 | 100 |
| 10.015 | 8.82507 | 6 |
| 12.505 | 7.07304 | 3.1 |
| 12.801 | 6.9098 | 3.9 |
| 13.447 | 6.57919 | 3.6 |
| 15.793 | 5.60677 | 6.9 |
| 16.511 | 5.36471 | 21.7 |
| 18.034 | 4.91498 | 9.6 |
| 18.796 | 4.7173 | 16.2 |
| 19.405 | 4.57058 | 16.5 |
| 19.864 | 4.46613 | 12.7 |
| 20.163 | 4.40059 | 10.3 |
| 20.554 | 4.31758 | 8 |

TABLE 2-continued

Observed X-ray diffraction peaks for Hydrate II of compound 2

| Angle 2-Theta ° | d value Angstrom | Intensity % |
|---|---|---|
| 21.18 | 4.19146 | 10.4 |
| 21.5 | 4.1297 | 4.8 |
| 21.816 | 4.07064 | 7.1 |
| 23.945 | 3.71326 | 6.7 |
| 24.42 | 3.64216 | 18.7 |
| 26.331 | 3.38204 | 4.4 |
| 26.696 | 3.33663 | 3.8 |

Figure 13:
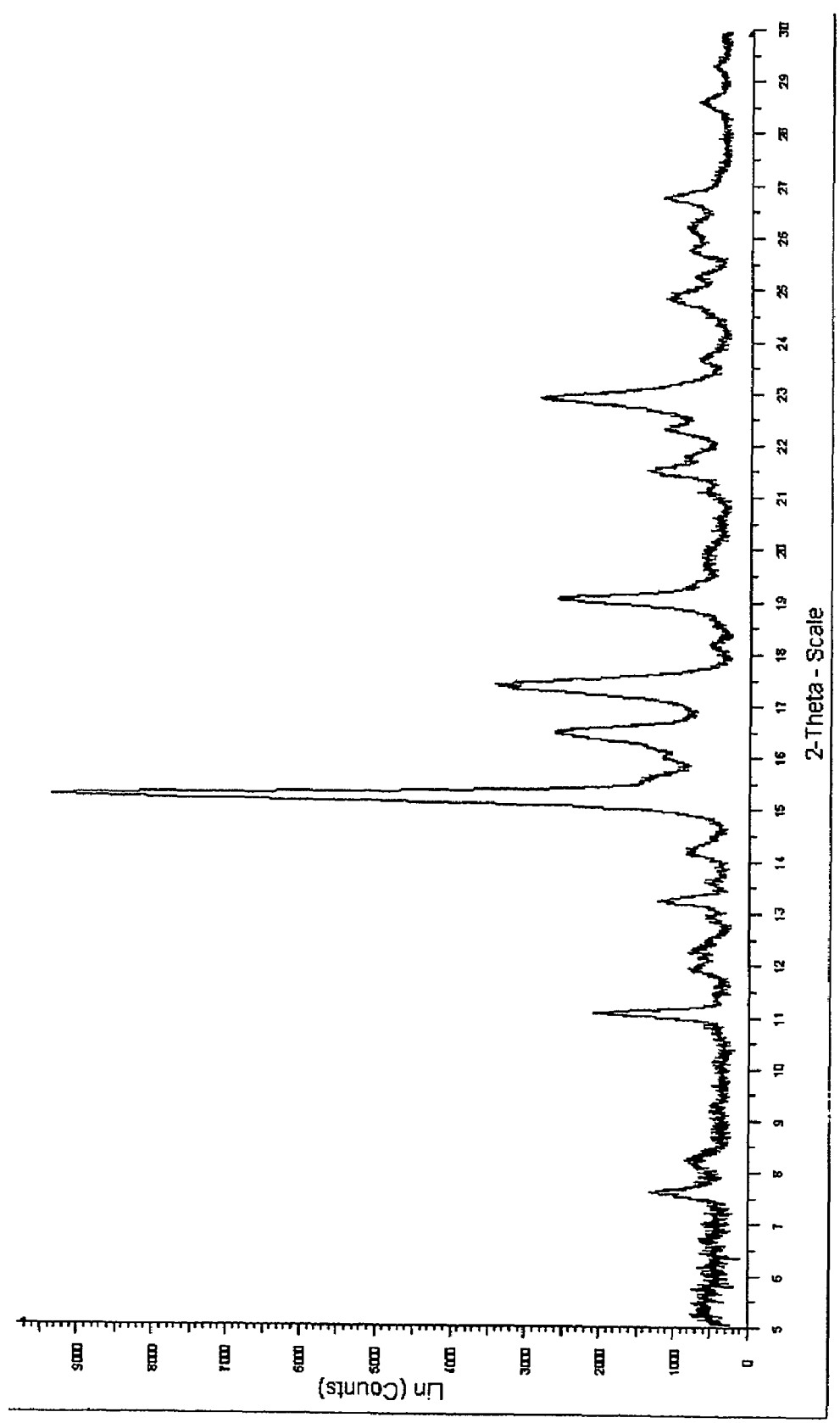
FIG. 13 depicts the X-ray powder diffraction pattern for the Methanolate of compound 2.

It has been found that compound 2 can exist in a variety of solvated crystal forms. In certain embodiments, the present invention provides a crystalline methanolate of compound 2. According to one aspect, the Methanolate of compound 2 has a powder X-ray diffraction pattern substantially similar to that depicted in FIG. 13. According to another embodiment, the Methanolate of compound 2 is characterized in that it has one or more peaks in its powder X-ray diffraction pattern selected from those at about 11.048, 15.211, 17.363, 19.047, and 22.897 degrees 2-theta. Methods for preparing the Methanolate of compound 2 are described infra.

Table 3 below sets out the X-ray diffraction peaks observed for the Methanolate of compound 2 wherein each value is in degrees 2-theta.

TABLE 3

Observed X-ray diffraction peaks for the Methanolate of compound 2

| Angle 2-Theta ° | d value Angstrom | Intensity % |
|---|---|---|
| 5.239 | 16.85421 | 3.1 |
| 5.422 | 16.28498 | 4.5 |
| 5.553 | 15.90081 | 3.5 |
| 5.724 | 15.42685 | 3.2 |
| 6.01 | 14.69341 | 3.2 |
| 6.645 | 13.29039 | 3.2 |
| 6.665 | 13.25056 | 3.3 |
| 7.591 | 11.63654 | 10.8 |
| 8.233 | 10.73127 | 5 |
| 11.048 | 8.00213 | 19.5 |
| 11.902 | 7.42993 | 5 |
| 13.232 | 6.68584 | 9.9 |
| 14.138 | 6.25942 | 5.6 |
| 14.215 | 6.2254 | 5 |
| 15.211 | 5.82005 | 100 |
| 16.012 | 5.53058 | 9.1 |
| 16.466 | 5.37913 | 24.6 |
| 17.363 | 5.10344 | 34.2 |
| 19.047 | 4.65574 | 25.2 |
| 19.329 | 4.58852 | 5.1 |
| 21.514 | 4.12704 | 11.7 |
| 22.313 | 3.98108 | 8.8 |
| 22.897 | 3.8809 | 27.6 |
| 23.641 | 3.76042 | 3.8 |
| 24.516 | 3.62806 | 3.1 |
| 24.815 | 3.5851 | 8.5 |
| 25.265 | 3.52217 | 4.7 |
| 25.769 | 3.45441 | 5.8 |
| 25.858 | 3.44277 | 4.9 |
| 26.778 | 3.32659 | 9.2 |
| 28.614 | 3.11719 | 4.4 |

Figure 14:
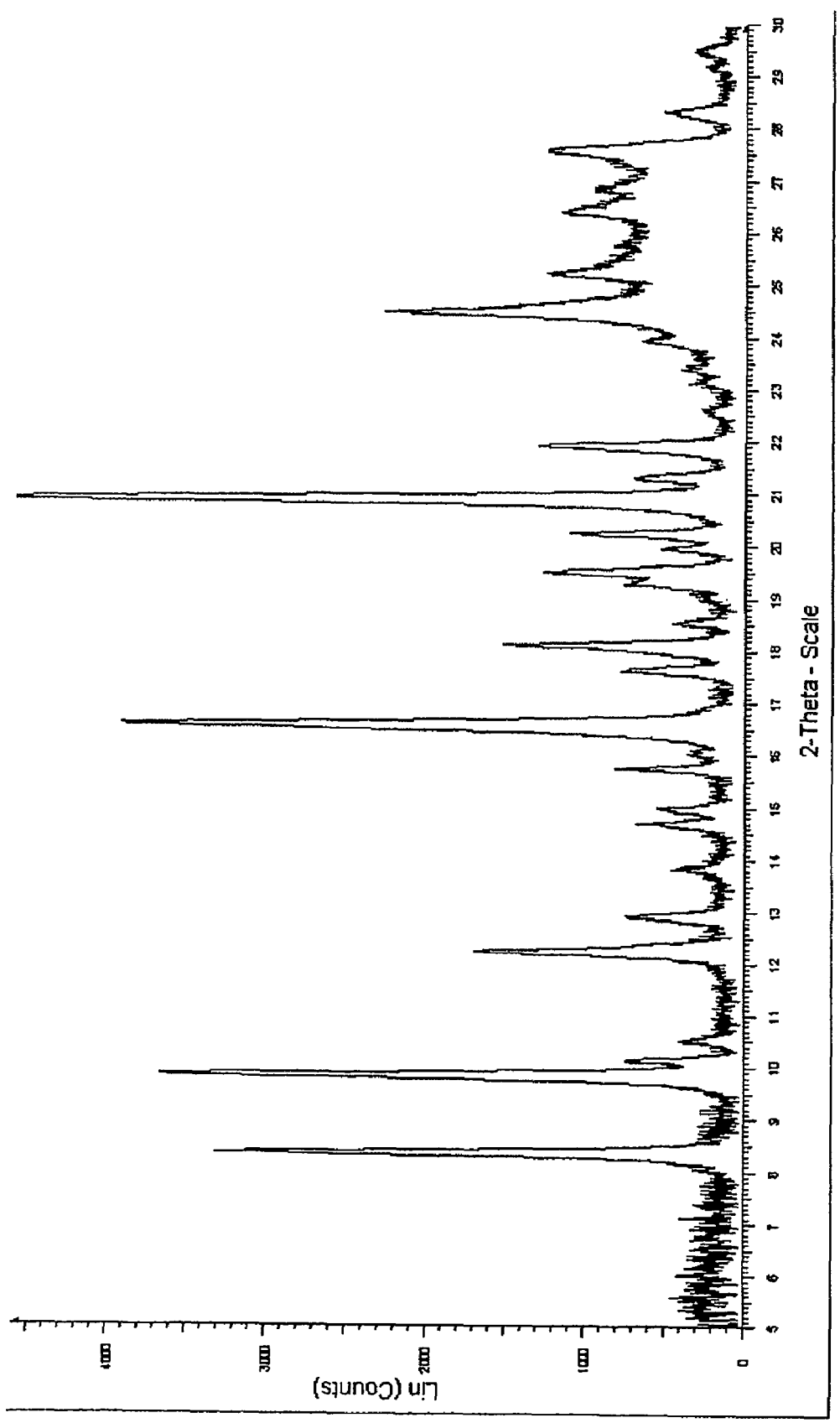
FIG. 14 depicts the X-ray powder diffraction pattern for Ethanolate I of compound 2.

In other embodiments, crystalline compound 2 is provided as an ethanolate. Two ethanolate forms of compound 2 have been identified. According to one aspect, the crystalline ethanolate of compound 2 is Ethanolate I and has a powder X-ray diffraction pattern substantially similar to that depicted in FIG. 14. According to another embodiment, Ethanolate I of compound 2 is characterized in that it has one or more peaks in its powder X-ray diffraction pattern selected from those at about 8.32, 9.81, 16.56, 20.88, and 24.47 degrees 2-theta. Methods for preparing Ethanolate I of compound 2 are described infra.

Table 4 below sets out the X-ray diffraction peaks observed for Ethanolate I of compound 2 wherein each value is in degrees 2-theta.

TABLE 4

Observed X-ray diffraction peaks for Ethanolate I of compound 2

| Angle 2-Theta ° | d value Angstrom | Intensity % |
|---|---|---|
| 5.17 | 17.10 | 5.00 |
| 5.55 | 15.91 | 7.60 |
| 5.68 | 15.54 | 5.40 |
| 5.84 | 15.12 | 5.10 |
| 5.98 | 14.76 | 3.70 |
| 6.47 | 13.66 | 4.70 |
| 6.68 | 13.22 | 4.10 |
| 7.10 | 12.44 | 6.20 |
| 7.28 | 12.13 | 3.10 |
| 7.42 | 11.91 | 3.00 |
| 8.00 | 11.04 | 4.40 |
| 8.32 | 10.62 | 70.10 |
| 8.84 | 9.99 | 3.50 |
| 9.81 | 9.01 | 77.70 |
| 10.10 | 8.75 | 13.50 |
| 10.51 | 8.41 | 5.90 |
| 12.20 | 7.25 | 33.60 |
| 12.90 | 6.86 | 13.60 |
| 13.80 | 6.41 | 7.50 |
| 14.68 | 6.03 | 12.30 |
| 14.96 | 5.92 | 9.40 |
| 15.73 | 5.63 | 15.50 |
| 16.56 | 5.35 | 83.30 |
| 17.62 | 5.03 | 13.70 |
| 18.10 | 4.90 | 30.70 |
| 18.54 | 4.78 | 7.60 |
| 19.28 | 4.60 | 13.60 |
| 19.49 | 4.55 | 25.40 |
| 19.96 | 4.44 | 8.50 |
| 20.24 | 4.38 | 21.50 |
| 20.88 | 4.25 | 100.00 |
| 21.28 | 4.17 | 12.80 |
| 21.91 | 4.05 | 26.00 |
| 22.61 | 3.93 | 3.70 |
| 23.13 | 3.84 | 5.20 |
| 23.42 | 3.79 | 4.60 |
| 23.93 | 3.72 | 11.80 |
| 24.47 | 3.63 | 47.30 |
| 25.22 | 3.53 | 24.80 |
| 26.39 | 3.37 | 22.40 |
| 26.81 | 3.32 | 18.10 |
| 27.56 | 3.23 | 24.90 |
| 28.31 | 3.15 | 8.70 |
| 29.20 | 3.06 | 3.10 |
| 29.50 | 3.03 | 4.40 |
| 29.57 | 3.02 | 3.50 |

Figure 15:
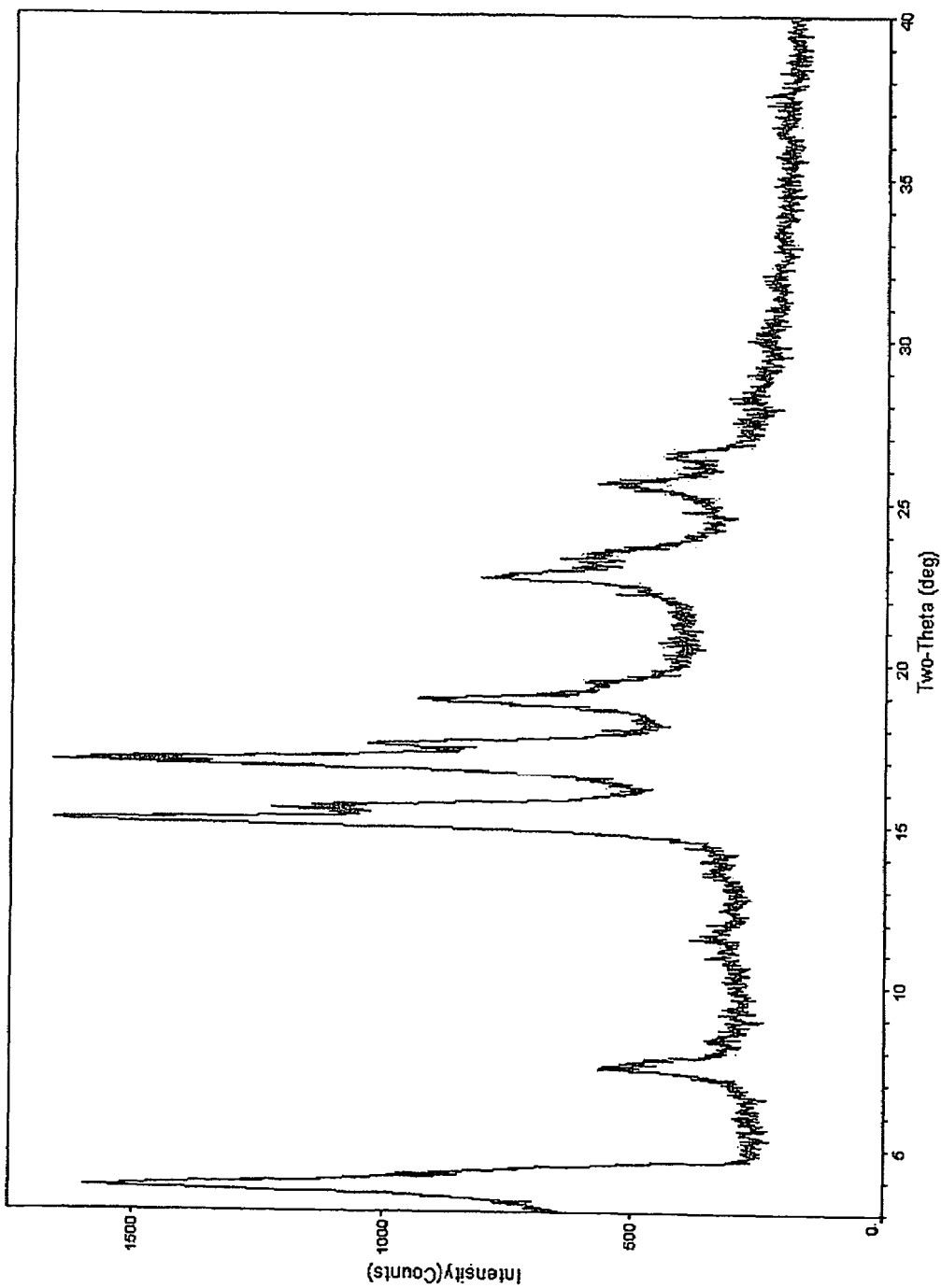
FIG. 15 depicts the X-ray powder diffraction pattern for Ethanolate II of compound 2.

In certain embodiments, the crystalline ethanolate of compound 2 is Ethanolate II and has a powder X-ray diffraction pattern substantially similar to that depicted in FIG. 15. According to another embodiment, Ethanolate II of compound 2 is characterized in that it has one or both peaks in its powder X-ray diffraction pattern selected from those at about 15.09 and 16.9 degrees 2-theta. Methods for preparing Ethanolate II of compound 2 are described infra.

Table 5 below sets out the X-ray diffraction peaks observed for Ethanolate II of compound 2 wherein each value is in degrees 2-theta.

TABLE 5

Observed X-ray diffraction peaks for Ethanolate II of compound 2

| Angle 2-Theta ° | d value Angstrom | Intensity % |
|---|---|---|
| 7.52 | 11.75 | 24.81 |
| 15.09 | 5.87 | 100.00 |
| 25.53 | 3.49 | 69.92 |
| 16.9 | 5.24 | 97.74 |
| 17.52 | 5.06 | 57.14 |
| 18.85 | 4.70 | 51.13 |
| 22.65 | 3.92 | 43.61 |
| 23.4 | 3.80 | 23.31 |
| 25.57 | 3.48 | 23.31 |
| 26.5 | 3.36 | 13.53 |

Figure 17:
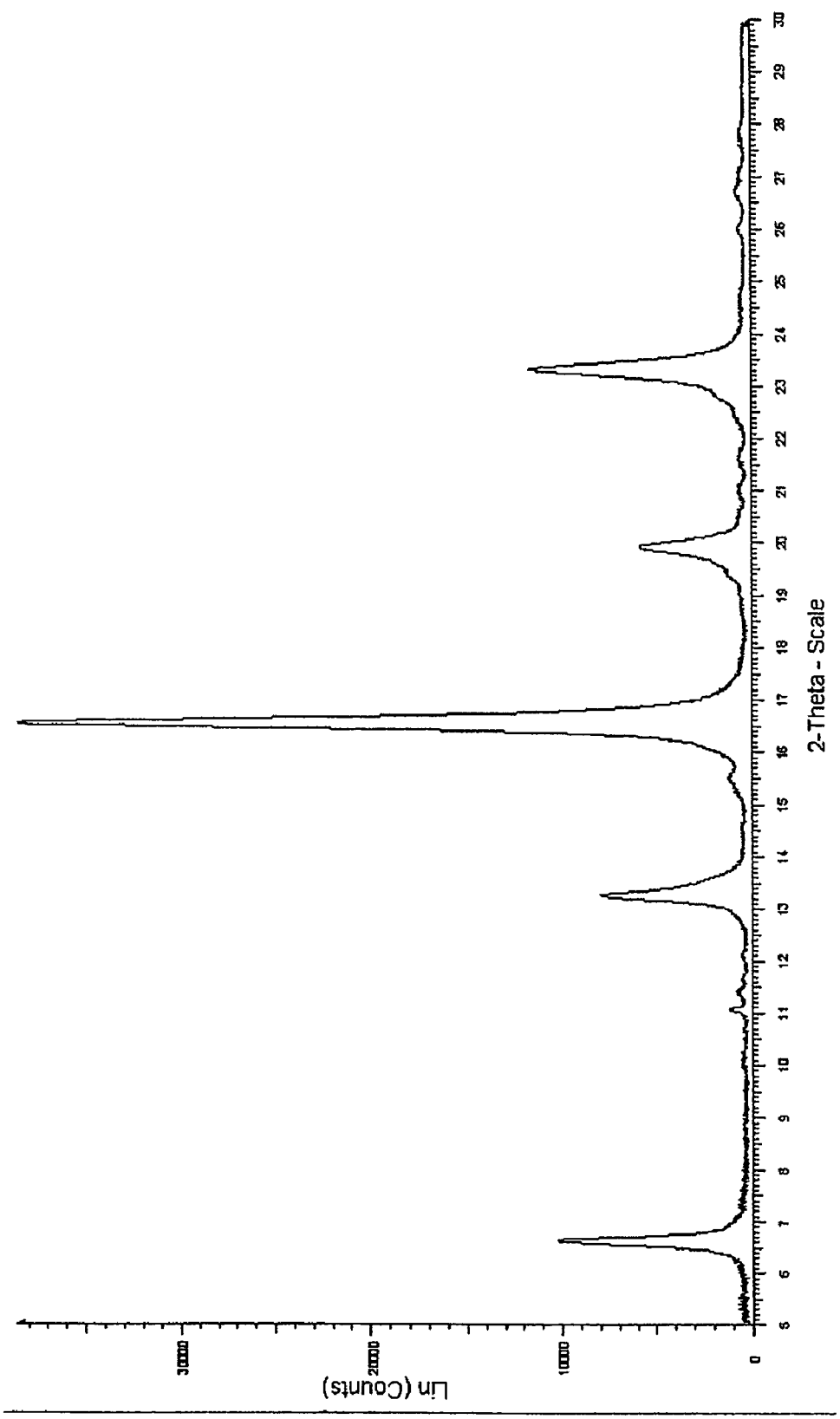
FIG. 17 depicts the X-ray powder diffraction pattern for Isopropanolate I (+DMF) of compound 2.
Figure 18:
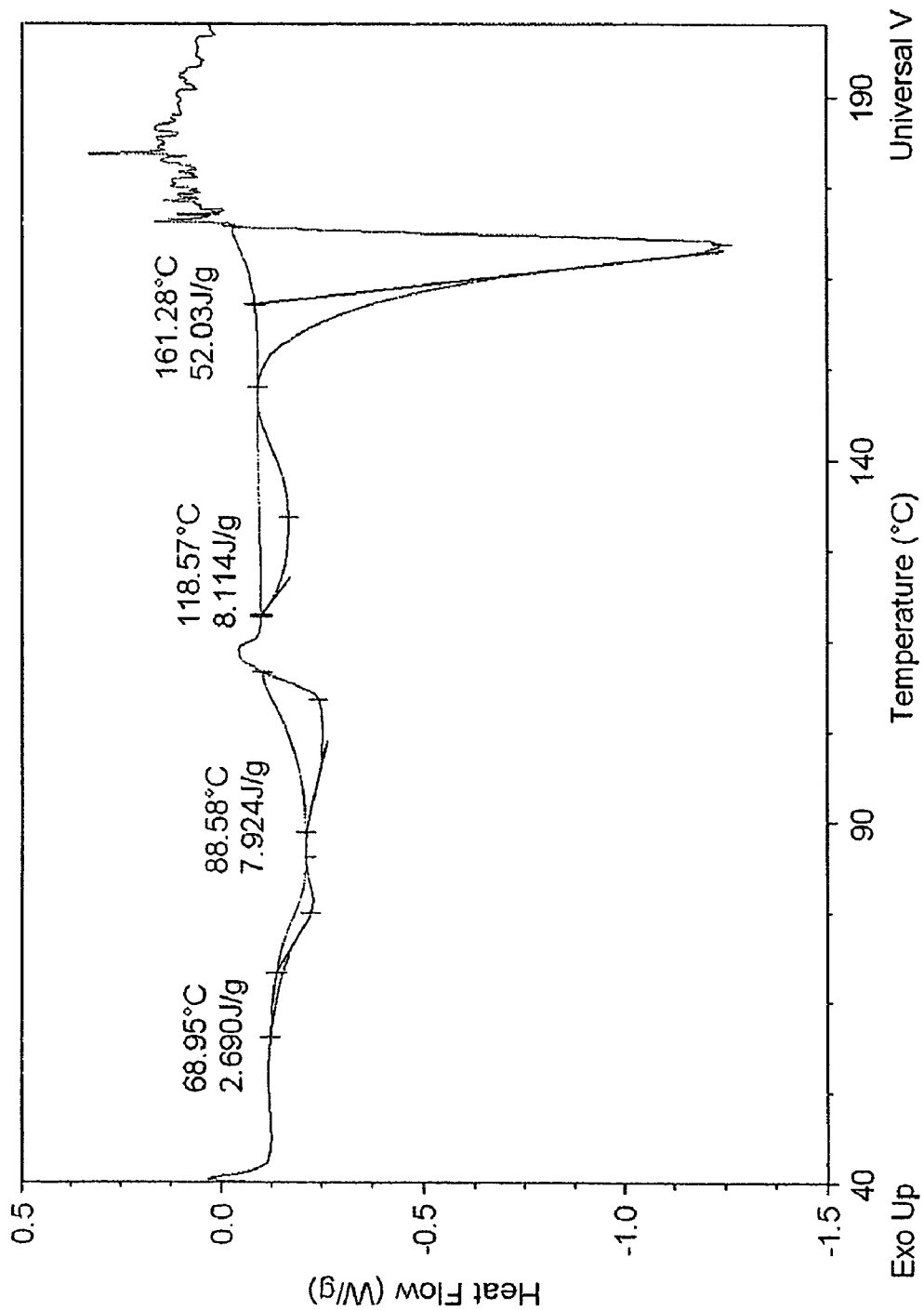
FIG. 18 depicts the DSC pattern for Isopropanolate I (+DMF) of compound 2.

In other embodiments, crystalline compound 2 is provided as an isopropanolate of compound 2. Two isopropanolate forms of compound 2 have been identified. According to one aspect, the crystalline isopropanolate of compound 2 is Isopropanolate I, which contains DMF. According to one aspect, Isopropanolate I of compound 2 has a powder X-ray diffraction pattern substantially similar to that depicted in FIG. 17 and/or a DSC pattern as depicted in FIG. 18. According to another embodiment, Isopropanolate I of compound 2 is characterized in that it has one or more peaks in its powder X-ray diffraction pattern selected from those at about 6.59, 13.23, 16.55, and 23.31 degrees 2-theta. Methods for preparing Isopropanolate I of compound 2 are described infra.

Table 6 below sets out the X-ray diffraction peaks observed for Isopropanolate I (+DMF) of compound 2 wherein each value is in degrees 2-theta.

TABLE 6

Observed X-ray diffraction peaks for Isopropanolate I (+DMF) of compound 2

| Angle 2-Theta ° | d value Angstrom | Intensity % |
|---|---|---|
| 6.59 | 13.41 | 25.80 |
| 11.04 | 8.00 | 2.10 |
| 13.23 | 6.69 | 19.50 |
| 15.50 | 5.71 | 2.50 |
| 16.55 | 5.35 | 100.00 |
| 19.91 | 4.46 | 14.40 |
| 23.31 | 3.81 | 29.50 |

Figure 19:
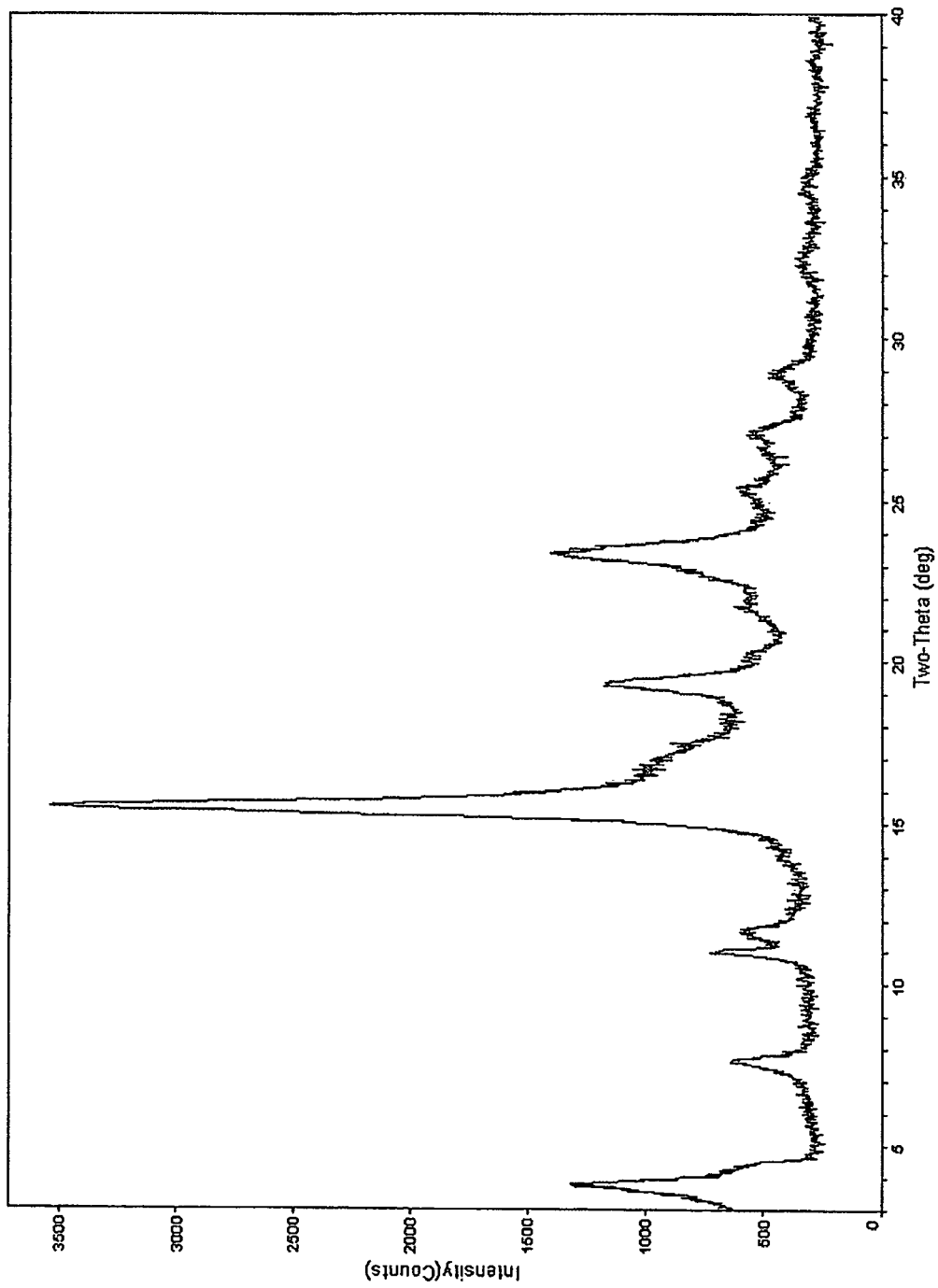
FIG. 19 depicts the X-ray powder diffraction pattern for Isopropanolate II of compound 2.

According to another aspect, the crystalline isopropanolate of compound 2 is Isopropanolate II, which contains no DMF. According to one aspect, Isopropanolate II of compound 2 has a powder X-ray diffraction pattern substantially similar to that depicted in FIG. 19. According to another embodiment, Isopropanolate II of compound 2 is characterized in that it has one or more peaks in its powder X-ray diffraction pattern selected from those at about 3.79, 15.54, and 23.32 degrees 2-theta. Methods for preparing Isopropanolate II of compound 2 are described infra.

Table 7 below sets out the X-ray diffraction peaks observed for Isopropanolate II of compound 2 wherein each value is in degrees 2-theta.

TABLE 7

Observed X-ray diffraction peaks for Isopropanolate II of compound 2

| Angle 2-Theta ° | d value Angstrom | Intensity % |
|---|---|---|
| 3.79 | 11.65 | 34.00 |
| 7.6186 | 5.81 | 16.77 |
| 11.07 | 4.01 | 19.72 |
| 11.71 | 3.80 | 16.26 |
| 15.54 | 2.88 | 100.00 |
| 19.36 | 2.32 | 33.34 |
| 23.32 | 1.95 | 39.38 |
| 25.37 | 1.80 | 17.46 |
| 27.08 | 1.69 | 15.60 |
| 28.93 | 1.59 | 13.48 |

In other embodiments, crystalline compound 2 is provided as an acetonate. According to one aspect, the Acetonate of compound 2 has a powder X-ray diffraction pattern substantially similar to that depicted in FIG. 21. According to another embodiment, the Acetonate of compound 2 is characterized in that it has one or more peaks in its powder X-ray diffraction pattern selected from those at about 11.04, 15.20, 15.47, and 20.81 degrees 2-theta. Methods for preparing the Acetonate of compound 2 are described infra.

Table 8 below sets out the X-ray diffraction peaks observed for the Acetonate of compound 2 wherein each value is in degrees 2-theta.

TABLE 8

Observed X-ray diffraction peaks for the Acetonate of compound 2

| Angle 2-Theta ° | d value Angstrom | Intensity % |
|---|---|---|
| 7.72 | 11.44 | 20.30 |
| 8.24 | 10.72 | 16.20 |
| 9.73 | 9.08 | 9.50 |
| 10.01 | 8.83 | 4.20 |
| 10.68 | 8.28 | 19.60 |
| 11.04 | 8.01 | 93.20 |
| 11.46 | 7.72 | 25.50 |
| 11.94 | 7.41 | 5.90 |
| 12.13 | 7.29 | 6.70 |
| 12.61 | 7.01 | 36.50 |
| 14.68 | 6.03 | 11.60 |
| 14.88 | 5.95 | 33.00 |
| 15.20 | 5.82 | 73.90 |
| 15.47 | 5.72 | 100.00 |
| 16.46 | 5.38 | 41.60 |
| 17.11 | 5.18 | 7.20 |
| 17.51 | 5.06 | 4.60 |
| 18.01 | 4.92 | 11.00 |
| 18.43 | 4.81 | 20.40 |
| 19.37 | 4.58 | 62.70 |
| 19.94 | 4.45 | 19.40 |
| 20.59 | 4.31 | 5.40 |
| 20.81 | 4.27 | 30.20 |
| 21.20 | 4.19 | 13.10 |
| 21.81 | 4.07 | 32.90 |
| 22.16 | 4.01 | 11.10 |
| 22.89 | 3.88 | 28.20 |
| 23.07 | 3.85 | 34.70 |
| 23.30 | 3.81 | 34.80 |
| 24.40 | 3.65 | 17.50 |
| 25.38 | 3.51 | 17.40 |
| 26.26 | 3.39 | 13.50 |
| 26.45 | 3.37 | 11.10 |
| 26.93 | 3.31 | 4.10 |
| 27.50 | 3.24 | 4.80 |
| 28.02 | 3.18 | 4.90 |
| 29.01 | 3.08 | 4.40 |

In certain embodiments, the present invention provides Form I of compound 2 comprising one or more additional solid forms of compound 2. In other embodiments, the present invention provides Form I of compound 2 comprising one or more of Form II, a hydrate of compound 2, a solvate of compound 2, or amorphous compound 2.

General Methods of Providing Compound 2:

Compound 1 is prepared according to the methods described in detail in PCT publication number WO 01/14330, the entirety of which is hereby incorporated herein by reference.

Another aspect of the present invention provides a method for preparing compound 2:

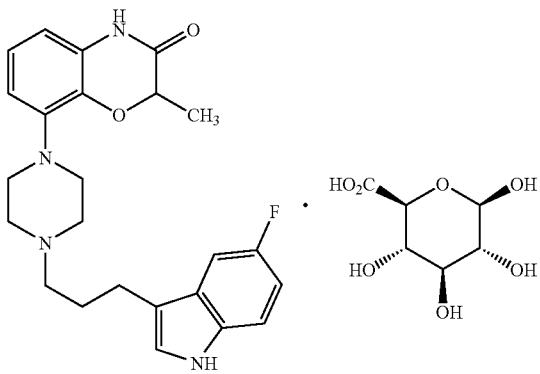

2 comprising the steps of:
providing compound 1:

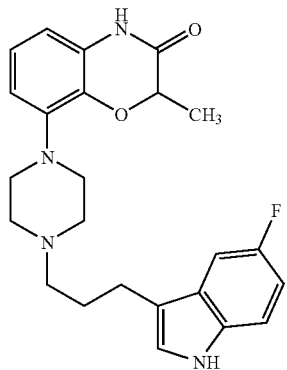

1 combining compound 1 with glucuronic acid in a suitable solvent; and
optionally isolating compound 2.

A suitable solvent may solubilize one or more of the reaction components, or, alternatively, the suitable solvent may facilitate the agitation of a suspension of one or more of the reaction components. Examples of suitable solvents useful in the present invention are a protic solvent, a polar aprotic solvent, or mixtures thereof. In certain embodiments, suitable solvents include an ether, an ester, an alcohol, a ketone, or a mixture thereof. In certain embodiments, the suitable solvent is methanol, ethanol, isopropanol, or acetone wherein said solvent is anhydrous or in combination with water or heptane. In other embodiments, suitable solvents include tetrahydrofuran, dimethylformamide, dimethylsulfoxide, glyme, diglyme, methyl t-butyl ether, t-butanol, n-butanol, and acetonitrile. In another embodiment, the suitable solvent is anhydrous ethanol.

According to another embodiment, the present invention provides a method for preparing compound 2:

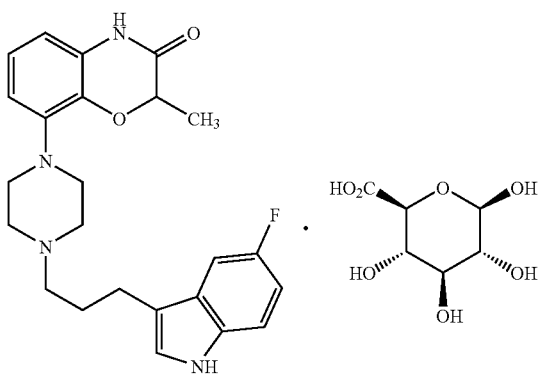

2 comprising the steps of:
combining compound 1:

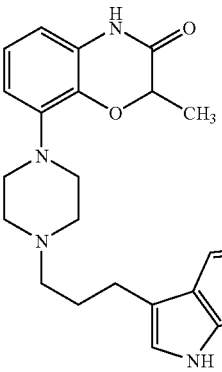

1 with a suitable solvent and optionally heating to form a solution thereof;
adding glucuronic acid to said solution; and
optionally isolating compound 2.

As described generally above, compound 1 is dissolved in a suitable solvent, optionally with heating. In certain embodiments compound 1 is dissolved at about 60° C. In other embodiments, compound 1 is dissolved at about 40° C. In yet other embodiments, compound 1 is dissolved at a temperature between about 40° C. and about 60° C. In still other embodiments, compound 1 is dissolved at the boiling temperature of the solvent. In other embodiments, compound 1 is dissolved without heating.

In certain embodiments, the solution of compound 1 is filtered prior to the addition of glucuronic acid. In other embodiments, the solution of compound 1 is not filtered prior to the addition of glucuronic acid.

In certain embodiments, where the solution of compound 1 was heated to any temperature between about 40° C. and about 60° C., the solution is subsequently cooled to any lower temperature that is between about 20° C. and about 40° C.

prior to the addition of glucuronic acid. In certain embodiments, where the solution of compound 1 was heated to any temperature between about 40° C. and about 60° C., the solution is not subsequently cooled to any lower temperature prior to the addition of glucuronic acid.

In certain embodiments, about 1 equivalent of glucuronic acid is added to compound 1 to afford compound 2. In other embodiments, less than 1 equivalent of glucuronic acid is added to compound 1 to afford compound 2. In yet other embodiments, greater than 1 equivalent of glucuronic acid is added to compound 1 to afford compound 2. In other embodiments, about 1.0 to about 1.2 equivalents of glucuronic acid is added to compound 1 to afford compound 2. In still other embodiments, about 0.9 to about 1.1 equivalents of glucuronic acid is added to compound 1 to afford compound 2. In another embodiment, about 0.99 to about 1.01 equivalents of glucuronic acid is added to compound 1 to afford compound 2.

It will be appreciated that the glucuronic acid may be added to the mixture of compound 1 and a suitable solvent in any suitable form. For example, the glucuronic acid may be added in solid form or as a solution or a suspension in a suitable solvent. The suitable solvent may be the same suitable solvent as that which is combined with compound 1 or may be a different solvent. According to one embodiment, the glucuronic acid is added in solid form. In certain embodiments, the glucuronic acid combined with a suitable solvent prior to adding to compound 1. According to another embodiment, the glucuronic acid is added as a solution in a suitable solvent. In other embodiments, the suitable solvent in which glucuronic acid is dissolved is a polar protic or polar aprotic solvent. Such solvents include water, alcohols, ethers, and ketones. Examples of such solvents include water, methanol, ethanol, isopropanol, acetone, tetrahydrofuran, dimethylformamide, dimethylsulfoxide, glyme, diglyme, methyl t-butyl ether, t-butanol, n-butanol, and acetonitrile. In certain embodiments the suitable solvent is selected from those above and is anhydrous. According to one embodiment, the glucuronic acid is dissolved in water.

In certain embodiments, the resulting mixture containing compound 2 is cooled. In certain embodiments where the mixture containing compound 2 is heated above about 20° C., the solution is allowed to cool to about 20° C. In other embodiments, the mixture containing compound 2 is cooled below 20° C.

In certain embodiments, compound 2 precipitates from the mixture. In another embodiment, compound 2 crystallizes from the mixture. In other embodiments, compound 2 crystallizes from solution following seeding of the solution (i.e., adding crystals of compound 2 to the solution).

Crystalline or amorphous compound 2 can precipitate out of the reaction mixture, or be generated by removal of part or all of the solvent through methods such as evaporation, distillation, filtration (ex. nanofiltration, ultrafiltration), reverse osmosis, absorption and reaction, by adding an anti-solvent such as heptane, by cooling or by different combinations of these methods.

As described generally above, compound 2 is optionally isolated. It will be appreciated that compound 2 may be isolated by any suitable physical means known to one of ordinary skill in the art. In certain embodiments, precipitated solid compound 2 is separated from the supernatant by filtration. In other embodiments, precipitated solid compound 2 is separated from the supernatant by decanting the supernatant. In certain embodiments, precipitated solid compound 2 is separated from the supernatant by filtration.

In certain embodiments, isolated compound 2 is dried in air. In other embodiments isolated compound 2 is dried under reduced pressure, optionally at elevated temperature.

According to another embodiment, the present invention provides a method for preparing compound 2:

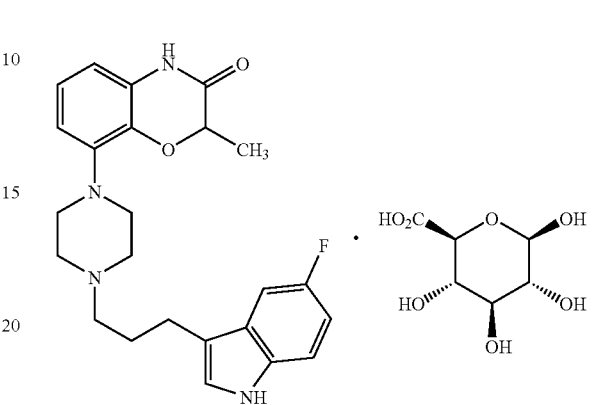

comprising the steps of:
  combining compound 1:

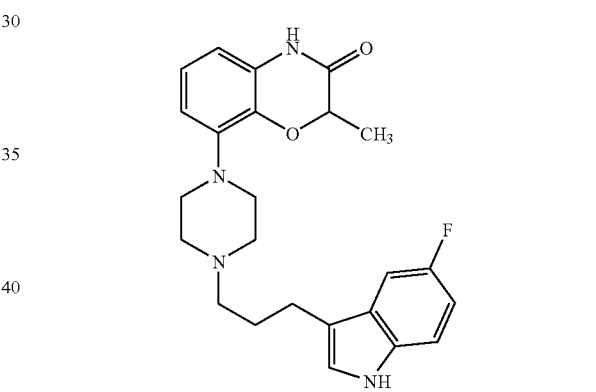

with a suitable solvent and heating to form a solution thereof;
  adding an aqueous solution of glucuronic acid to said solution; and
  optionally isolating compound 2.

In certain embodiments, the method for preparing compound 2 further comprises the step of distilling the reaction mixture. According to another aspect of the present invention, the reaction mixture is distilled while adding additional solvent such that the water content is decreased. In other embodiments, the method further comprises the step of cooling the resulting slurry comprising compound 2 and isolating compound 2 by suitable physical means.

According to one embodiment, the molar ratio of glucuronic acid to compound 1 obtained is about 0.5 to about 1.0. In other embodiments, the ratio of glucuronic acid to compound 1 obtained is between about 0.8 and about 2.0. In certain embodiments, the ratio is between about 0.9 and about 1.2. In other embodiments, the ratio is between about 0.94 and about 1.06. In still other embodiments, the ratio is between about 0.94 and about 0.95.

Uses of Compounds and Pharmaceutically Acceptable Compositions

As discussed above, the present invention provides compound 2 which is useful as a modulator of D receptors, 5HT receptors, 5HT reuptake, and prostaglandin synthesis, and shows utility in clinically relevant models for psychoses, depression, stress/anxiety, and Parkinson's disease. In certain embodiments, the present compound is useful as a modulator of one or more of $D_2$ receptor subtype, 5HT reuptake, or prostaglandin synthesis. In other embodiments, the present compound is useful for the treatment of psychoses, depression, stress/anxiety, and Parkinson's disease.

Accordingly, in another aspect of the present invention, pharmaceutically acceptable compositions are provided, wherein these compositions comprise compound 2, and optionally comprise a pharmaceutically acceptable carrier, adjuvant, or vehicle. In certain embodiments, these compositions optionally further comprise one or more additional therapeutic agents.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the salt of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

In yet another aspect, a method for treating or lessening the severity of a disorder associated with the modulation of D receptors, 5HT receptors, 5HT reuptake, and prostaglandin synthesis, and/or for treating or lessening the severity of psychoses, depression, stress/anxiety, and/or Parkinson's disease is provided, comprising administering an effective amount of compound 2, or a pharmaceutically acceptable composition thereof, to a subject in need thereof. In certain embodiments of the present invention an "effective amount" of the compound or pharmaceutically acceptable composition is that amount effective for treating or lessening the severity of a disorder associated with the modulation of D receptors, 5HT receptors, 5HT reuptake, and prostaglandin synthesis, and/or for treating or lessening the severity of psychoses, depression, stress/anxiety, and/or Parkinson's disease. In other embodiments, an "effective amount" of a compound is an amount which acts as a modulator of one or more of D receptors, 5HT receptors, 5HT reuptake, and prostaglandin synthesis An "effective amount" of a compound can achieve a desired therapeutic and/or prophylactic effect, such as an amount which results in the prevention of, or a decrease in the symptoms associated with, a disease associated with one or more of D receptor, 5HT receptor, 5HT reuptake, and prostaglandin synthesis modulation, and/or with psychoses, depression, stress/anxiety, and/or Parkinson's disease.

The compound and compositions, according to the method of the present invention, may be administered using any amount and any route of administration effective for treating or lessening the severity of a disorder associated with modulation of one or more of D receptors, 5HT receptors, 5HT reuptake, and prostaglandin synthesis, and/or for treating or lessening the severity of psychoses, depression, stress/anxiety, and/or Parkinson's disease. The exact amount required will vary from subject to subject, depending on the species, age, and general condition of the subject, the severity of the infection, the particular agent, its mode of administration, and the like. The salt of the invention is preferably formulated in dosage unit form (e.g., as a tablet, capsule, or ampoule) for ease of administration and uniformity of dosage. The expression "dosage unit form" as used herein refers to a physically discrete unit of agent appropriate for the patient to be treated. It will be understood, however, that the total daily usage of the salt and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, nasally, rectally, parenterally, intracisternally, intravaginally, intraperitoneally, topically (as by powders, ointments, or drops), bucally, or the like, depending on the severity of the infection being treated. In certain embodiments, the salt of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral or nasal administration include, but are not limited to, pharmaceutically acceptable emulsions, microemulsions, solutions, suspensions, aerosols, gels, syrups, and elixirs. In addition to the active salt, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively the sealed container may be a unitary dispensing device such as a single dose nasal inhaler or an aerosol dispenser fitted with a metering valve which is intended for disposal once the contents of the container have been exhausted. Where the dosage form comprises an aerosol dispenser, it will contain a pharmaceutically acceptable propellant. The aerosol dosage forms can also take the form of a pump-atomiser.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

Advantageously, compound 2, as described herein, has enhanced water solubility. Accordingly, the present compound is useful for intravascular and intramuscular delivery. Without wishing to be bound by any particular theory, it is believed that the enhanced solubility of compound 2 would allow for a smaller injection volume resulting in less pain and discomfort for the patient. Accordingly, the present invention also relates to an injectable formulation for intravascular or intramuscular delivery.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Typical parenteral compositions consist of a solution or suspension of the compound or physiologically acceptable salt in a sterile aqueous carrier or non-aqueous or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

Compositions for rectal or vaginal administration are conveniently in the form of suppositories, pessaries, vaginal tabs, foams, or enemas. Compositions for rectal or vaginal administration are preferably suppositories which can be prepared by mixing the salt of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium salts, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Compositions suitable for buccal or sublingual administration include tablets, lozenges and pastilles, wherein the active ingredient is formulated with a carrier such as sugar and acacia, tragacanth, or gelatin and glycerin.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient (s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

Compound 2 can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms compound 2 may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Compositions for oral administration may be designed to protect the active ingredient against degradation as it passes through the alimentary tract, for example by an outer coating of the formulation on a tablet or capsule.

In another embodiment, compound 2, is be provided in an extended (or "delayed" or "sustained") release composition. This delayed release composition comprises compound 2 in combination with a delayed release component. This composition allows targeted release of compound 2 into the lower gastrointestinal tract; for example into the small intestine, the large intestine, the colon and/or the rectum. In certain embodiments, the delayed release composition comprising compound 2 further comprises an enteric or pH dependent coating such as cellulose acetate phthalates and other phthalates (e.g. polyvinyl acetate phthalate, methacrylates (Eudragits)). Alternatively, the delayed release composition provides controlled release to the small intestine and/or colon by the provision of pH sensitive methacrylate coatings, pH sensitive polymeric microspheres, or polymers which undergo degradation by hydrolysis. The delayed release composition can be formulated with hydrophobic or gelling excipients or coatings. Colonic delivery can further be provided by coatings which are digested by bacterial enzymes such as amylose or pectin, by pH dependent polymers, by hydrogel plugs swelling with time (Pulsincap), by time dependent hydrogel coatings and/or by acrylic acid linked to azoaromatic bonds coatings.

In certain embodiments, the delayed release compositions of the present invention comprise hypromellose, microcrystalline cellulose, and a lubricant. The mixture of compound 2, hypromellose and microcrystalline cellulose may be formulated into a tablet or capsule for oral administration. In certain embodiments, the mixture is granulated and pressed into tablets.

In other embodiments, the delayed release compositions of the present invention are provided in a multiparticulate formulation. A mixture of compound 2 and a suitable polymer is granulated to form pellets which are coated. In certain embodiments, the pellets are seal coated with a non-functional coating. In other embodiments, the pellets are first seal coated with a non-functional coating and then coated with a functional coating.

As used herein the term "non-functional coating" is a coating that does not effect the release rate of the drug. Examples of a non-functional coat include hydroxypropyl cellulose, hypromellose or polyvinyl alcohol. In certain embodiments, the non-functional coating is Opadry® Clear, which contains, hydroxypropyl methylcellulose and polyethylene glycol.

As used herein, the term "functional coating" is a coating that affects the release rate of the drug from the dosage form. Examples of a functional coating include ethylcellulose and polymethacrylate derivatives (Eudragits).

Accordingly, another embodiment provides a multiparticulate formulation comprising a pellet core comprising compound 2, a non-functional seal coating and a functional seal coating.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compositions may contain from 0.1% to 99% (w/w) preferably from 0.1-60% (w/w), more preferably 0.2-20% by weight and most preferably 0.25 to 12% (w/w) of compound 2, depending on the method of administration.

As described generally above, the salt of the present invention is useful as modulators of one or more of D receptors, 5HT receptors, 5HT reuptake, and prostaglandin synthesis and thus the invention further relates to a method for treating (e.g., palliative, curative, prophylactic) or lessening the severity of a disease or disorder associated with modulation of one or more of D receptors, 5HT receptors, 5HT reuptake, and prostaglandin synthesis.

In one embodiment, compound 2 is a modulator of one or more of D receptors, 5HT receptors, 5HT reuptake, and prostaglandin synthesis, and thus, without wishing to be bound by any particular theory, the present compound and compositions are particularly useful for treating or lessening the severity of a disease, condition, or disorder where modulation of one or more of D receptors, 5HT receptors, 5HT reuptake, and prostaglandin synthesis is implicated in the disease, condition, or disorder. When modulation of one or more of D receptors, 5HT receptors, 5HT reuptake, and prostaglandin synthesis is implicated in a particular disease, condition, or disorder, the disease, condition, or disorder may also be referred to as a "D receptor, 5HT receptor, 5HT reuptake, or prostaglandin synthesis-mediated disease" or disease symptom.

In certain embodiments, the salts and compositions of the present invention provide a method for treating or lessening the severity of one or more disorders including, but not limited to, Parkinson's disease, psychoses (e.g., schizophrenia, mania, psychotic depression, and bipolar disorder), depression, stress/anxiety, Alzheimer's disease, Huntington's disease, panic disorder, obsessive compulsive disorder, eating disorders, drug addiction, social phobias, aggression or agitation, migraine, scleroderma and Raynaud's phenomenon, emesis, GI tract disorders related to the regulation of peristalsis, RLS, and prolactin secretion arising from tumours of the pituitary gland, wherein said method comprises administering to a patient compound 2, or a composition thereof.

It will also be appreciated that the salt and pharmaceutically acceptable compositions of the present invention can be employed in combination therapies, that is, compound 2, and compositions thereof, can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents which are normally administered to treat or prevent a particular disease, or condition, are known as "appropriate for the disease, or condition, being treated".

The amount of additional therapeutic agent present in the compositions of this invention will be no more than the amount that would normally be administered in a composition comprising that therapeutic agent as the only active agent. In certain embodiments, the amount of additional therapeutic agent in the presently disclosed compositions will range from about 50% to 100% of the amount normally present in a composition comprising that agent as the only therapeutically active agent.

Another aspect of the invention relates to modulating D receptors, 5HT receptors, 5HT reuptake, and prostaglandin synthesis activity in a biological sample or a patient, which method comprises administering to the patient, or contacting the biological sample with, compound 2, or a composition thereof. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Modulation of D receptors, 5HT receptors, 5HT reuptake, and prostaglandin synthesis activity in a biological sample is useful for a variety of purposes that are known to one of skill in the art. Examples of such purposes include, but are not limited to, biological assays.

The amount of compound 2 effective to treat a disorder as set out above depends on the nature and severity of the disorder being treated and the weight of the patient in need thereof. However, a single unit dose for a 70 kg adult will normally contain 0.01 to 100 mg, for example 0.1 to 50 mg, preferably 0.5 to 16 mg of the compound of the invention per day. Unit doses may be administered once or more than once a day, for example, 2, 3 or 4 times a day, usually 1 to 3 times a day, more preferably 1 or 2 times per day. It will be appreciated that the dose ranges set out above provided guidance for the administration of compound 2 to an adult. The amount to be administered to for example, an infant or a baby can be determined by a medical practitioner or person skilled in the art and can be lower or the same as that administered to an adult. The unit dose is preferably provided in the form of a capsule or a tablet.

All features of each of the aspects of the invention apply to all other aspects mutatis mutandis.

In order that the invention described herein may be more fully understood, the following examples are set forth. It should be understood that these examples are for illustrative purposes only and are not to be construed as limiting this invention in any manner.

EXAMPLES

General Procedures

Powder X-ray diffraction patterns were obtained on a Rigaku Miniflex Diffraction System (Rigaku MSC Inc.). The powder samples were deposited on a zero-background polished silicon sample holder. A normal focus copper X-ray tube at 0.45 kW equipped with a Ni Kβ filter scanning at 2 degrees/minute from 3.00 to 40.00 degree 2-theta was used as the X-ray source. The data processing was done using Jade 6.0 software.

Proton Nuclear Magnetic Resonance ($^1$H NMR) spectra were obtained on a Bruker model Avance DRX-500 MHz NMR spectrometer, equipped with a 5mm QNP probe. About 5-25 mg of each compound was dissolved in 0.6 mL DMSO-d6 (99.9% D), containing 0.05% TMS as an internal reference. $^1$H NMR spectra were recorded at 500.133 MHz, using a 30 degree pulse, with a pulse delay of 20 seconds, 32 k data points, 64 scans. An exponential window function with 0.3 Hz line broadening was applied to 16 k data points to process data without zero-filling and TMS was referred as 0.00 ppm. Quantitative $^{13}$C NMR was acquired at 125.7 MHz, using inverted gated decoupling, a 30 degree pulse, and 8 seconds delay.

DSC data were obtained on a TA Q1000 Differential Scanning Calorimeter. The instrument heated the sample for 40° C. to 200° C. at 10° C./min with a nitrogen purge of 50 mL/min.

Example 1

Preparation of Compound 2 (Form I)

Figure 2:
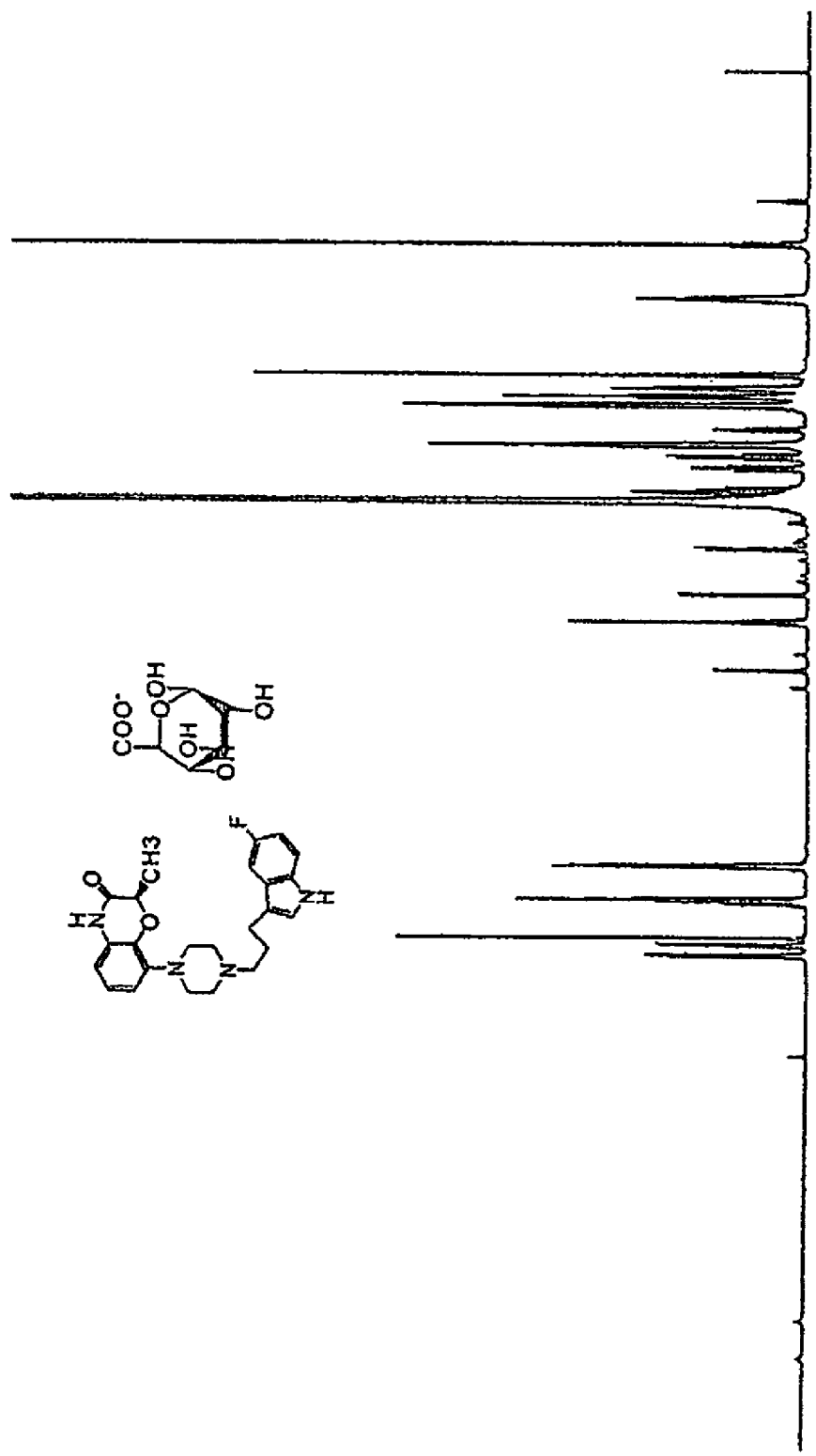
FIG. 2 depicts the $^1$H NMR spectrum of compound 2.
Figure 3:
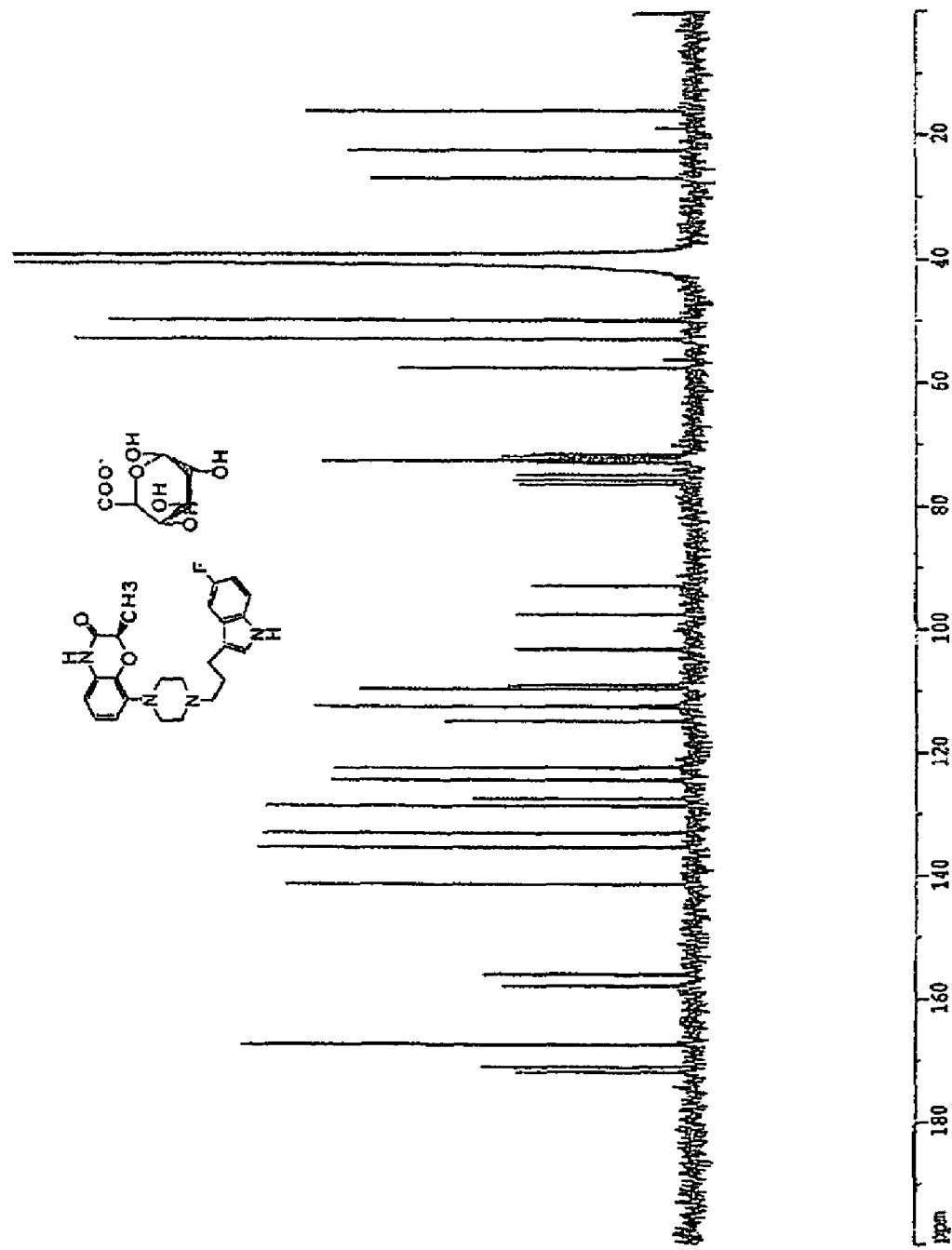
FIG. 3 depicts the $^{13}$C NMR spectrum of compound 2.
Figure 4:
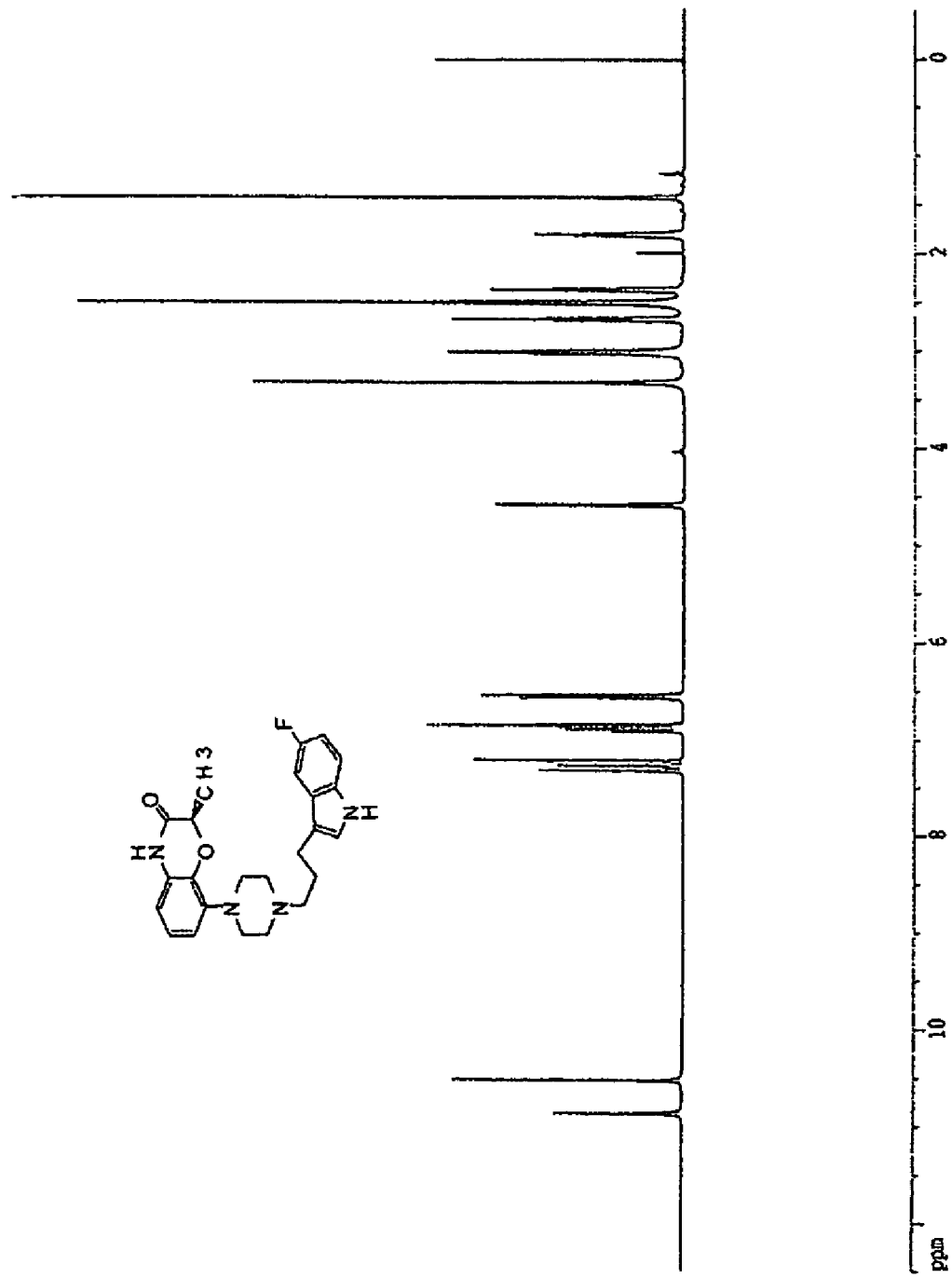
FIG. 4 depicts the $^1$H NMR spectrum of compound 1.

Compound 1 (500 mg) was slurried in 20 mL anhydrous ethanol and heated to 60° C. to obtain a clear solution. The solution was filtered through a 0.45 μm filter and cooled to 40° C. To this solution, 275 mg of glucuronic acid (1.2 equiv) was added. A thin white slurry was obtained. The slurry was cooled to 20° C. and stirred with a magnet stirrer for 16 hours. The slurry was filtered and the resulting solid phase was air-dried at room temperature and analyzed by X-ray diffraction (see FIG. 1) and optical microscopy and found to be crystalline compound 2. FIG. 2 depicts the $^1$H NMR spectrum obtained for compound 2. FIG. 3 depicts the $^{13}$C NMR spectrum obtained for compound 2, and FIG. 4 depicts the $^1$H NMR spectrum obtained for compound 1.

Example 2

Preparation of Compound 2 (Form I) by Reactive Distillation from Ethanol/Water

Figure 6:
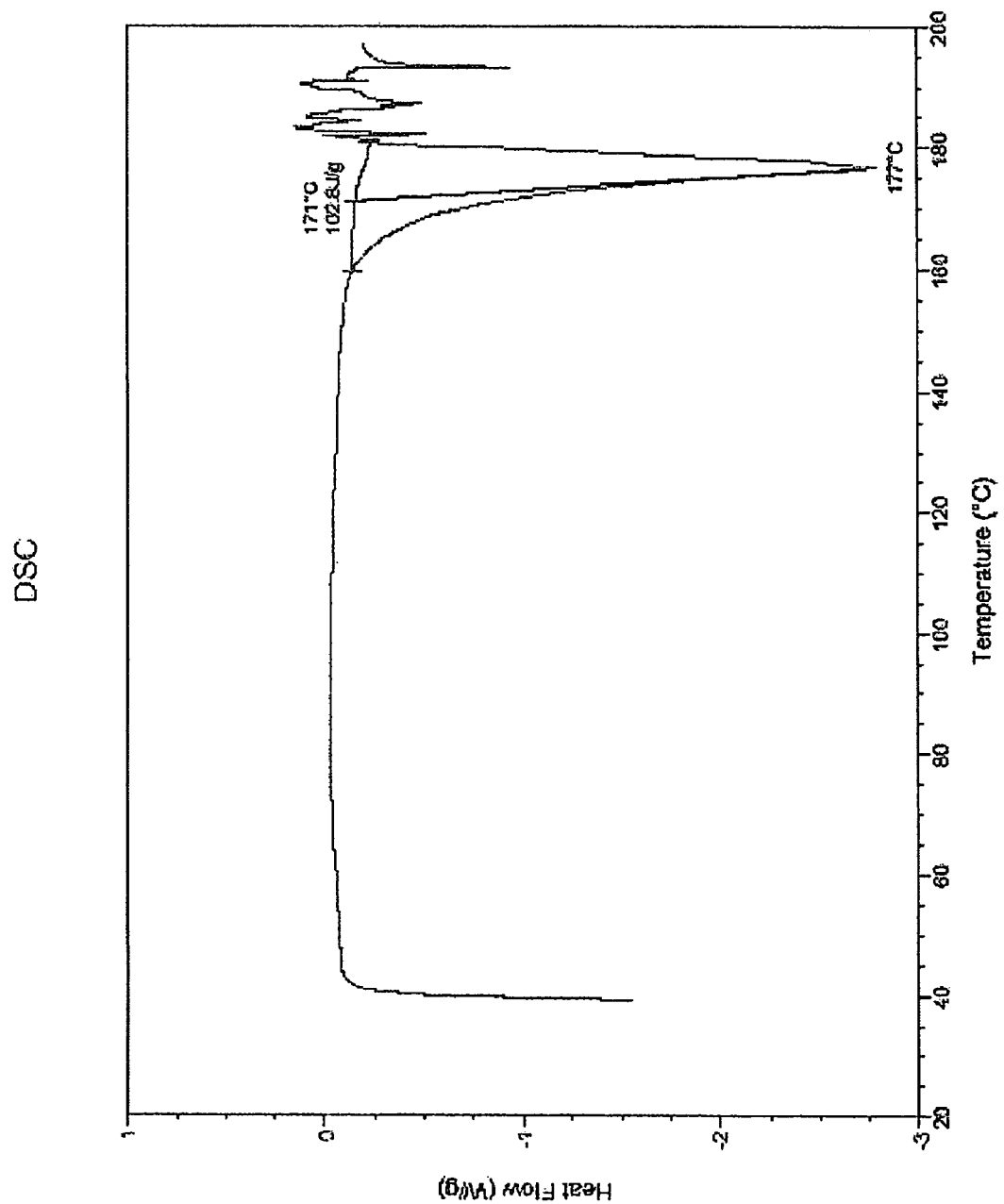
FIG. 6 depicts the DSC pattern for Form I of compound 2.

D-glucuronic acid (4.6 g) was added into 25 mL water and dissolved at room temperature. Compound 1 (10 g) was added into 320 mL anhydrous ethanol and heated to 50-70° C. to obtain a clear solution. The prepared glucuronic acid (1 eq) water solution was added to the solution of freebase and ethanol solution. The solution remained clear and was then naturally cooled to room temperature and stirred for 16 hours. The resulting solution was azeotropically distilled at 78° C. Approximately 400 mL total anhydrous ethanol was added back into the solution, 200 mL every 0.5 hours during distillation. White solid precipitated during distillation. The distillation was stopped when 600 mL solution was distilled out, and 150 mL of white slurry was left. The slurry was filtrated and dried overnight at 50° C. with vacuum to afford compound 2. The final product (12 g, 84% yield) was crystalline as characterized by powder X-Ray Diffraction (FIG. 5) and DSC (FIG. 6).

Table 9 below sets out the X-ray diffraction peaks observed for Form I of compound 2 wherein each value is in degrees 2-theta.

TABLE 9

Observed X-ray diffraction peaks for compound 2 (Form I)
2-Theta 12.158
14.460
15.541
16.399
17.599
19.204
20.018
22.340
23.296
25.740
29.658

Example 3

Preparation of Compound 2 (Form I) by Heterogeneous Reaction in Ethanol

Compound 1 (500 mg) was dissolved in 70 mL anhydrous ethanol at room temperature. 230 mg of glucuronic acid (1.0 eq) was added to the free base solution to form a slurry. The slurry as stirred for 16 hours at room temperature and was then filtered. The solid phase was dried under vacuum at 50° C. to afford compound 2. The final product (235 mg, 32.2% yield) was characterized by X-ray diffraction, DSC and NMR spectroscopy.

Example 4

Preparation of Compound 2 (Form I) by Heterogeneous Reaction at 60° C. in Ethanol Compound 1 (400 mg) was slurried in 13 mL anhydrous ethanol and heated to 60° C. to obtain a clear solution. The solution was filtered through a 0.45 μm filter and cooled to 40° C. To this solution, 202 mg of glucuronic acid (1.1 eq) was added. A thin white slurry was obtained. The slurry was cooled to 20° C. and stirred with a magnetic stirrer for 16 hours. The slurry was filtered and the resulting solid phase (224 mg, 38%) was dried at 50° C. with vacuum.

Example 5

General Method for Preparing Compound 2 (Form I)

Add 25.3 kg of ethanol to 1 kg of compound 1 and heat mixture to 60° C. Add 2 kg of water to 0.46 kg of glucuronic acid; stir to allow all acid to dissolve in water. Add the glucuronic acid solution to the free base solution. Check for clear solution. Cool the solution to 50° C. Filter the reaction solution at 50 C through a 0.5 μm filter. Cool the reaction solution to 24° C. and stir slowly for 16 hours. Heat the reaction solution to 78° C. to start distillation. Distill 15.8 kg of solution, add 15.8 kg of ethanol, distill 15.8 kg of solution, add 15.8 kg of ethanol and finally distill 20 L of solution. (Distilled 60 L, added 40 L, remaining solution volume 15.5 L). Cool reaction to 20° C. in 1 hour and hold reaction at 20° C. for 1 hour. Filter mother liquor and wash cake twice with 4.0 kg (8 kg total) of ethanol. Dry the Cake at 50° C. under vacuum for 12 hours.

Example 6

Alternative Method for Preparing Compound 2 (Form I) from Acetonitrile

In another method to prepare Form I, amorphous compound 2 was slurried in acetonitrile at room temperature for three days. The amorphous solid transformed into the neat crystal form of compound 2 (Form I).

Example 7

Preparation of Amorphous Compound 2

Figure 8:
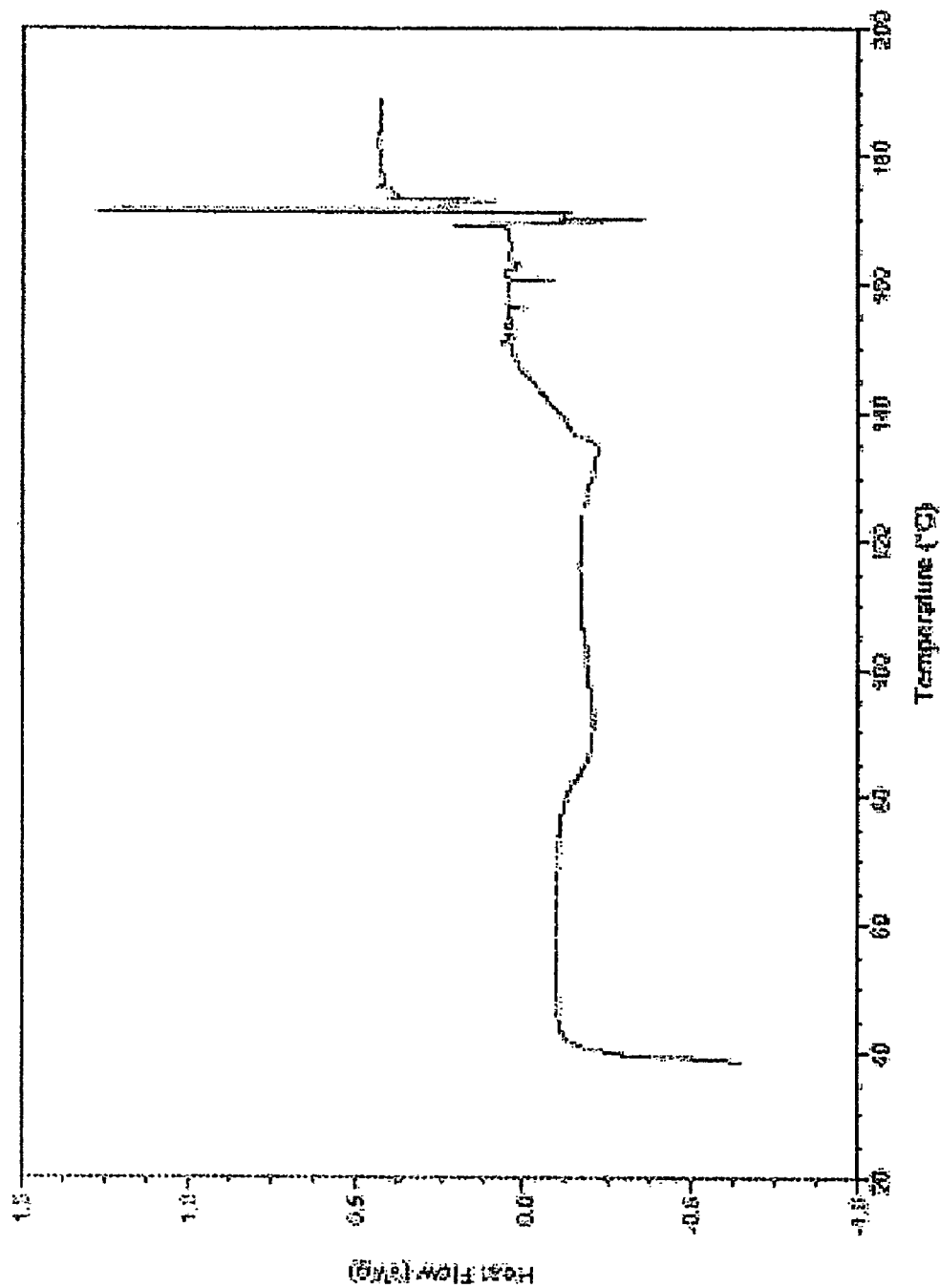
FIG. 8 depicts the DSC pattern for amorphous compound 2.

Method A: 0.92 g D-glucuronic acid was added into 5 mL water and dissolved at room temperature. 2 g SLV-314 freebase (32797-94-01) was added into 20 mL acetone and heated to 40-50° C. to obtain a clear solution. The prepared glucuronic acid (1 eq) water solution was added to this solution and stirred. The solution remained clear and was then naturally cooled to room temperature and stirred for 16 hours. The resulting solution was distilled at ~56° C. 50 mL of acetone was added back into the solution in two intervals during distillation. Some white solid briefly appeared during distillation and then dissolved. The distillation was stopped when 35 mL solution was distilled out, and 35 mL of clear solution left. The solvent was evaporated in a dryer at 50° C. under vacuum generating a light brown dry amorphous solid, which was characterized by powder X-Ray Diffraction (FIG. 7) and DSC (FIG. 8).

Method B: Compound 2 was dissolved in 32 volumes ethanol and 4 volumes water at elevated temperature. The solvent was evaporated at atmospheric pressure by heating to reflux temperature. A gel was produced. Gel was dried under vacuum and 50° C. An amorphous solid was produced.

Example 8

Preparation of Compound 2 (Form II)

Form I of compound 2 converts to Form II upon slurrying Form I in a variety of solvents. This conversion occurs over time at room temperature or at elevated temperature. Form I was reslurried in toluene, acetone, tBME, acetonitrile or isopropyl acetate at room temperature or 50° C. for one to two weeks. It was found that elevated temperature facilitated the conversion. Formation of Form II was monitored by the characteristic peak at 18.7 degrees two-theta in the powder X-ray diffraction pattern.

Example 9

Preparation of compound 2 Hydrate I

Figure 10:
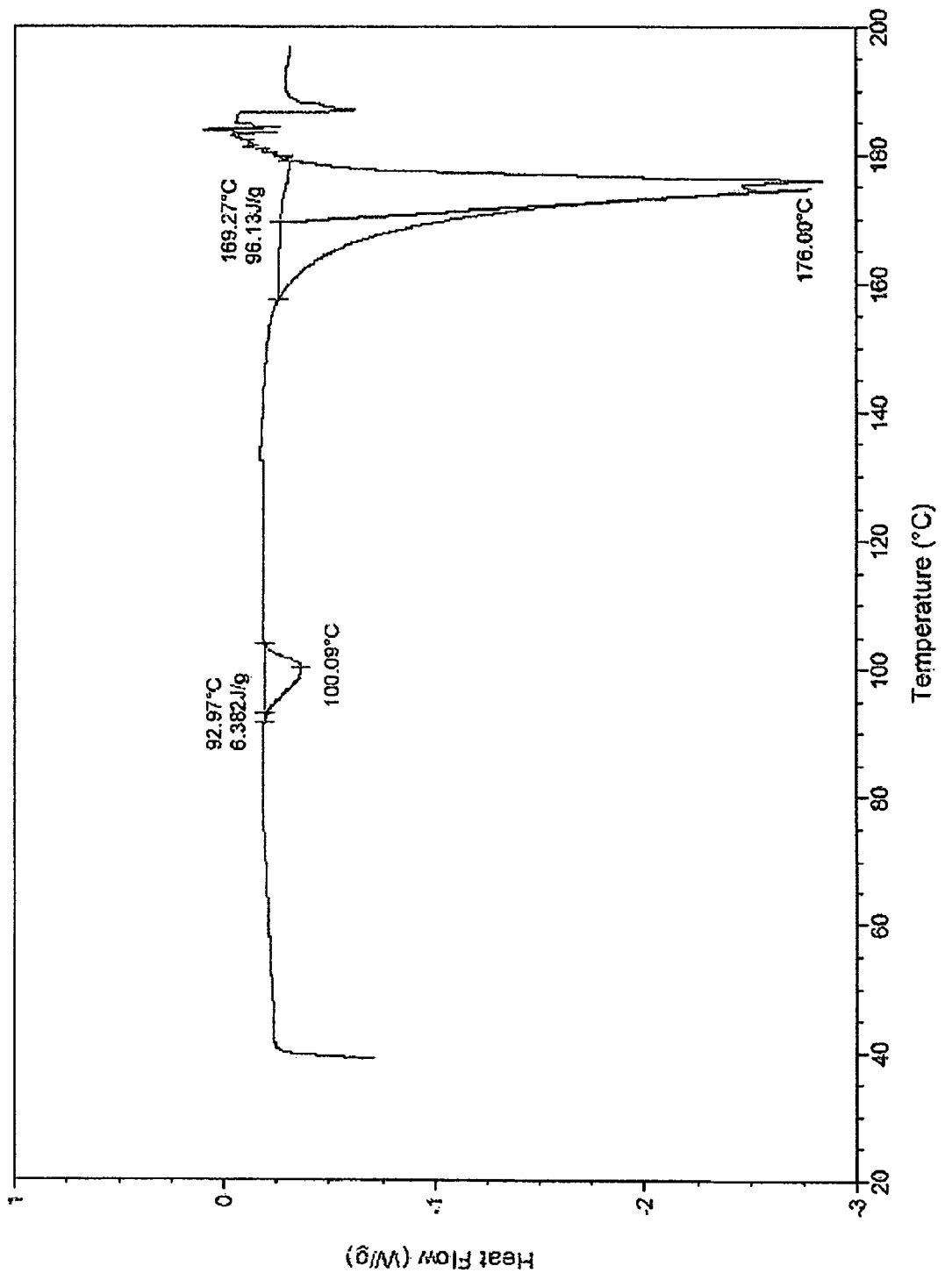
FIG. 10 depicts the DSC pattern for Hydrate I of compound 2.

Compound 2 Form I was reslurried in water for more than 2 weeks at room temperature or 50° C. Overall conversion was very slow to afford the title compound as a mixture of Form I and Hydrate I characterized by powder X-ray crystal diffraction and DSC. See FIGS. 9 and 10.

Example 10

Preparation of Compound 2 Hydrate II

Figure 12:
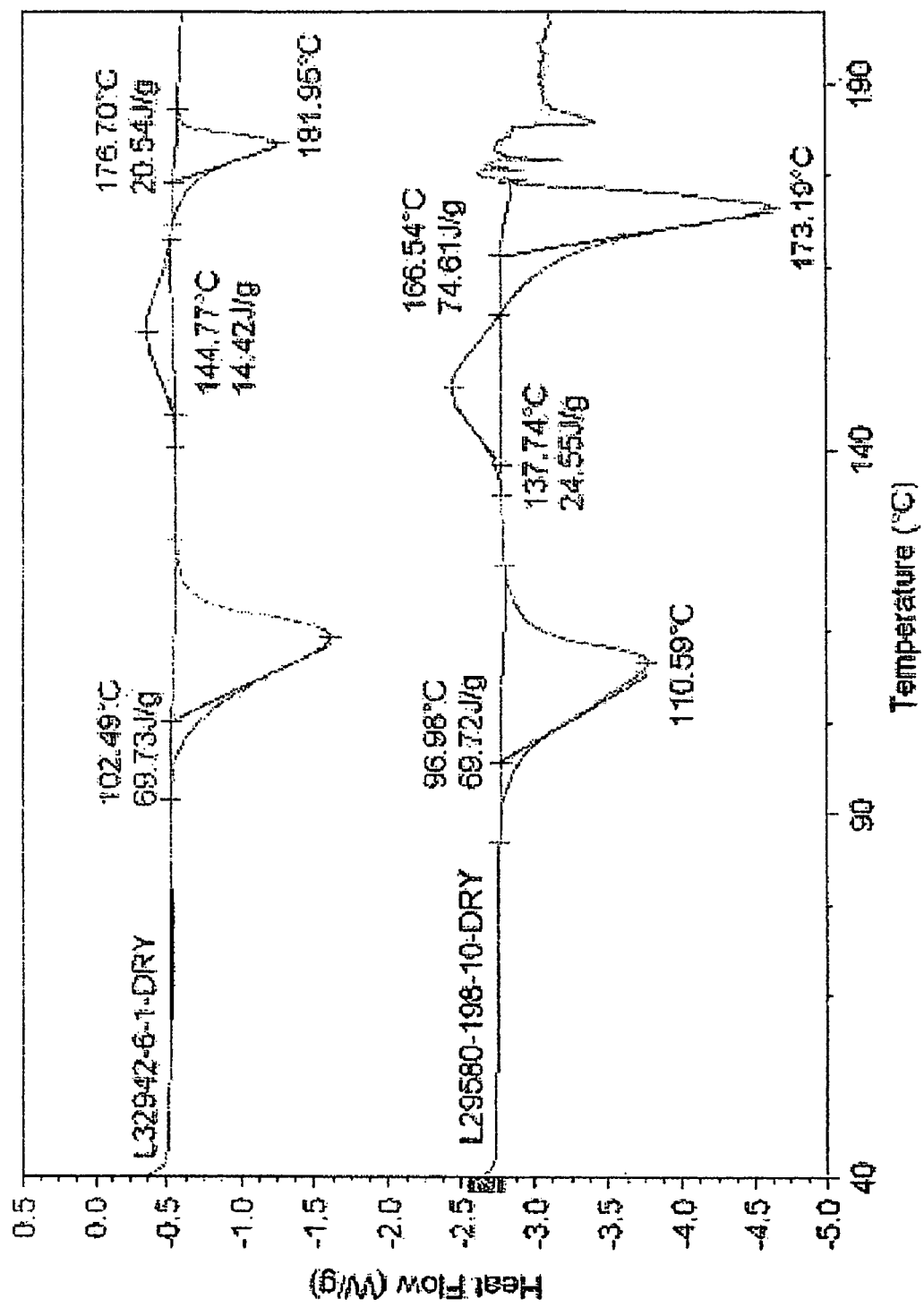
FIG. 12 depicts the DSC patterns for Hydrate I (top scan) and Hydrate II (bottom scan) of compound 2.

Amorphous compound 2 was dissolved in 6 volume of water at room temperature and the compound allowed crystallize at room temperature. The resulting suspension was stirred overnight and the title compound collected by filtration and characterized by powder X-ray crystal diffraction and DSC. See FIGS. 11 and 12, respectively.

Example 11

Preparation of Solvates of Compound 2

Methanolate

Amorphous compound 2 was dissolved in 6 volumes of methanol at room temperature and allowed to crystallize at room temperature. The resulting mixture was stirred overnight and the solid Methanolate collected by filtration. See FIG. 13. The Methanolate was found to be unstable under drying and converted to Form I.

Ethanolate

Compound 1 was dissolved in 32 volumes of ethanol 1J1 at elevated temperature. A stoichiometric amount of glucuronic acid, dissolved in 3-4 volumes of water, was added at once. Nucleation started immediately. The resulting mixture was stirred on ice for 30 minutes then left overnight without stirring. The title compound was collected by filtration and characterized by powder X-ray crystal diffraction as Ethanolate I. See FIGS. 14. The Ethanolate I converted to Form I upon drying.

Figure 16:
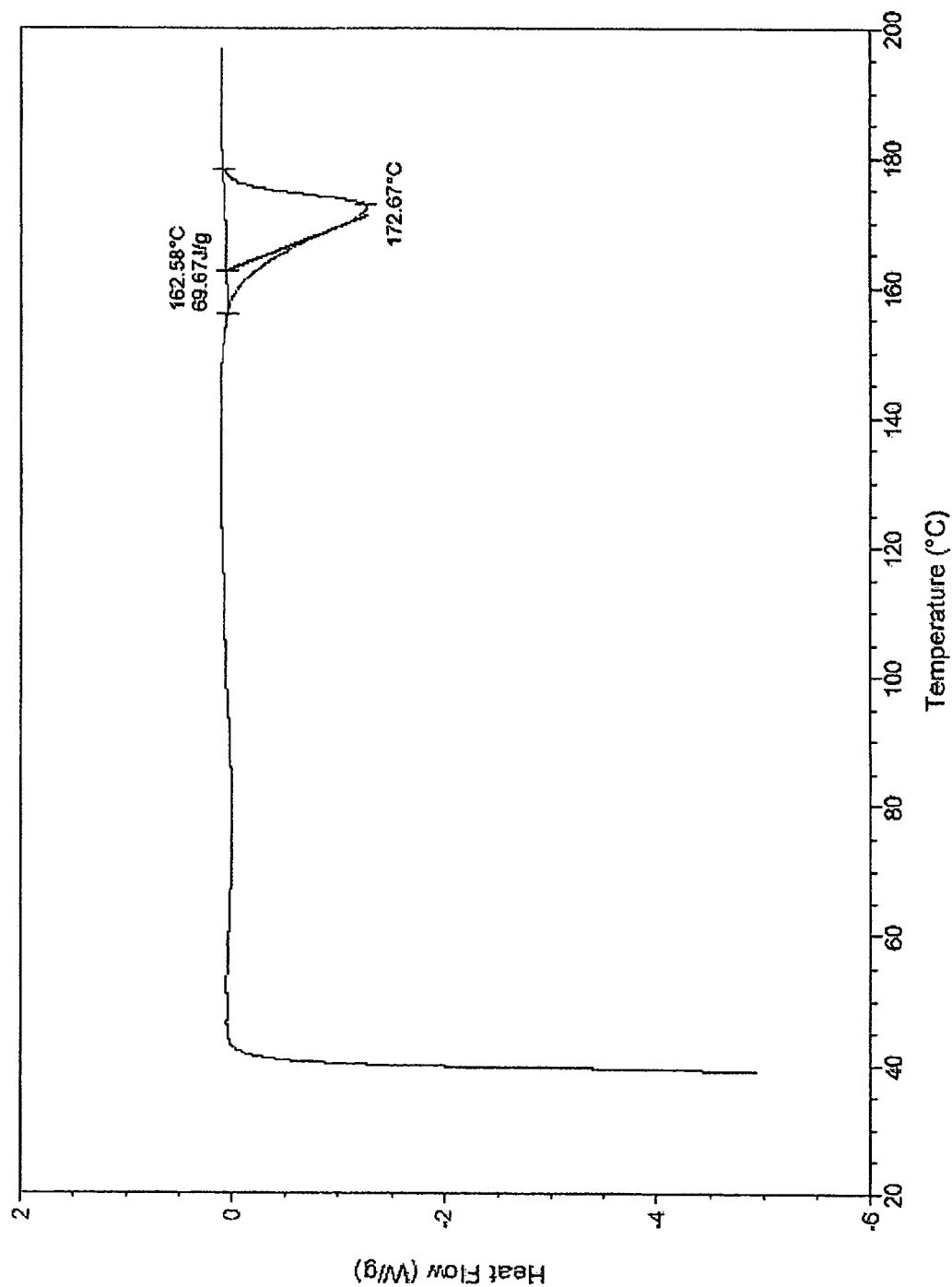
FIG. 16 depicts the DSC pattern for Ethanolate II of compound 2.

Alternatively, a second ethanolate of compound 2, Ethanolate II, was prepared by dissolving amorphous compound 2 in 6 volumes of ethanol 1J1 (ethanol-ethyl acetate). The mixture was stirred overnight and Ethanolate II was collected by filtration. FIG. 15 depicts the powder X-ray diffraction pattern of Ethanolate II and FIG. 16 depicts the DCS of Ethanolate II.

Isopropanolate

Compound 2 was dissolved in 10 volumes of DMF at room temperature. 60 volumes of IPA were added over 10 minutes. The resulting mixture was stirred for 30 minutes. The Isopropanolate I compound was collected by filtration and characterized by powder X-ray crystal diffraction and DSC. See FIGS. 17 and 18. The wet filter cake showed the Isopropanolate+DMF. Drying the sample destructed the structure to amorphous compound that contained solvent.

Figure 20:
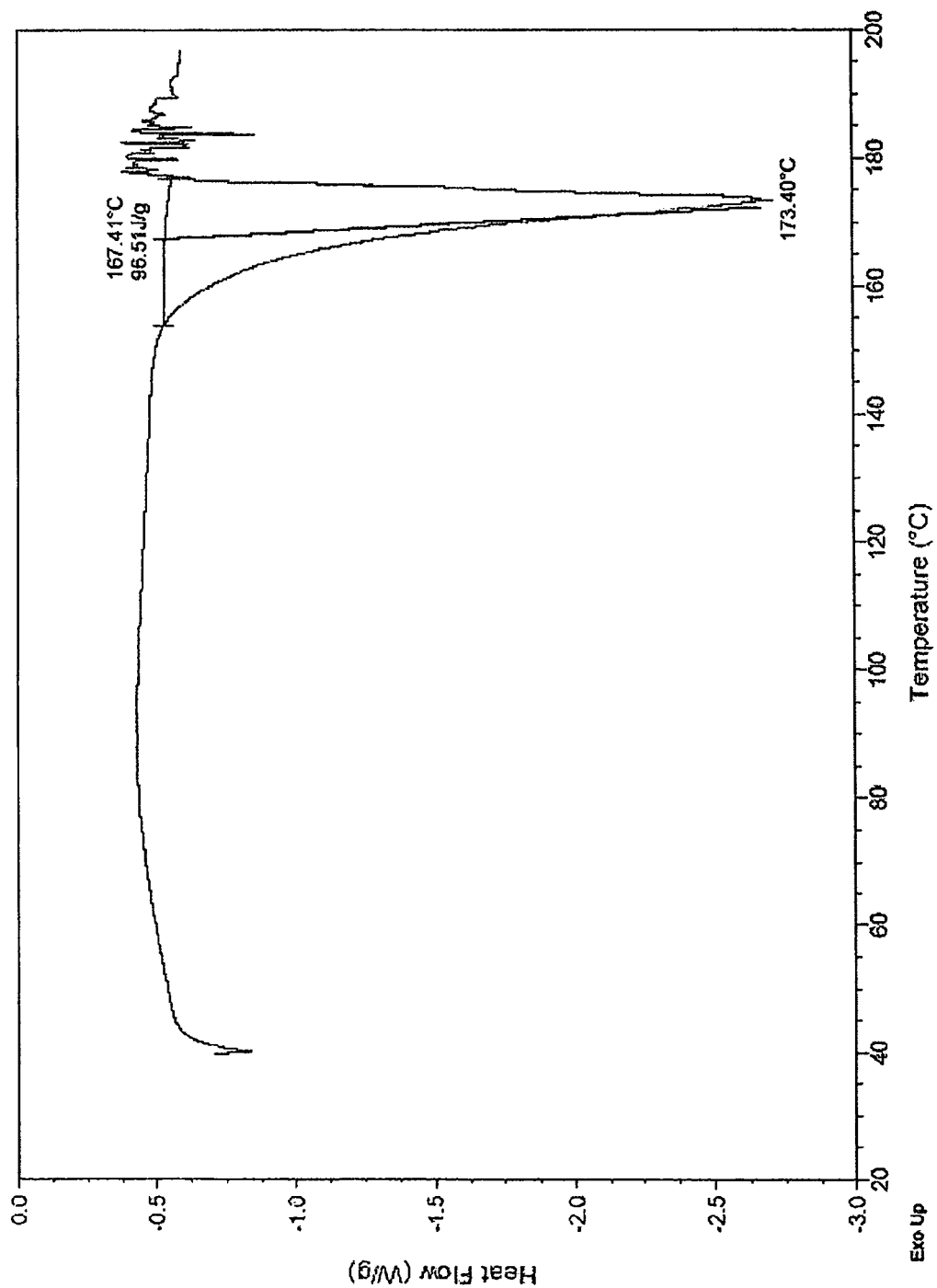
FIG. 20 depicts the DSC pattern for Isopropanolate II of compound 2.

Alternatively, a second isopropanolate, Isopropanolate II, of compound 2 was prepared by slurrying amorphous compound 2 in IPA at room temperature for 2 or 3 days. See FIGS. 19 and 20, which depict the powder X-ray diffraction pattern and DSC trace, respectively.

Acetonate

Figure 21:
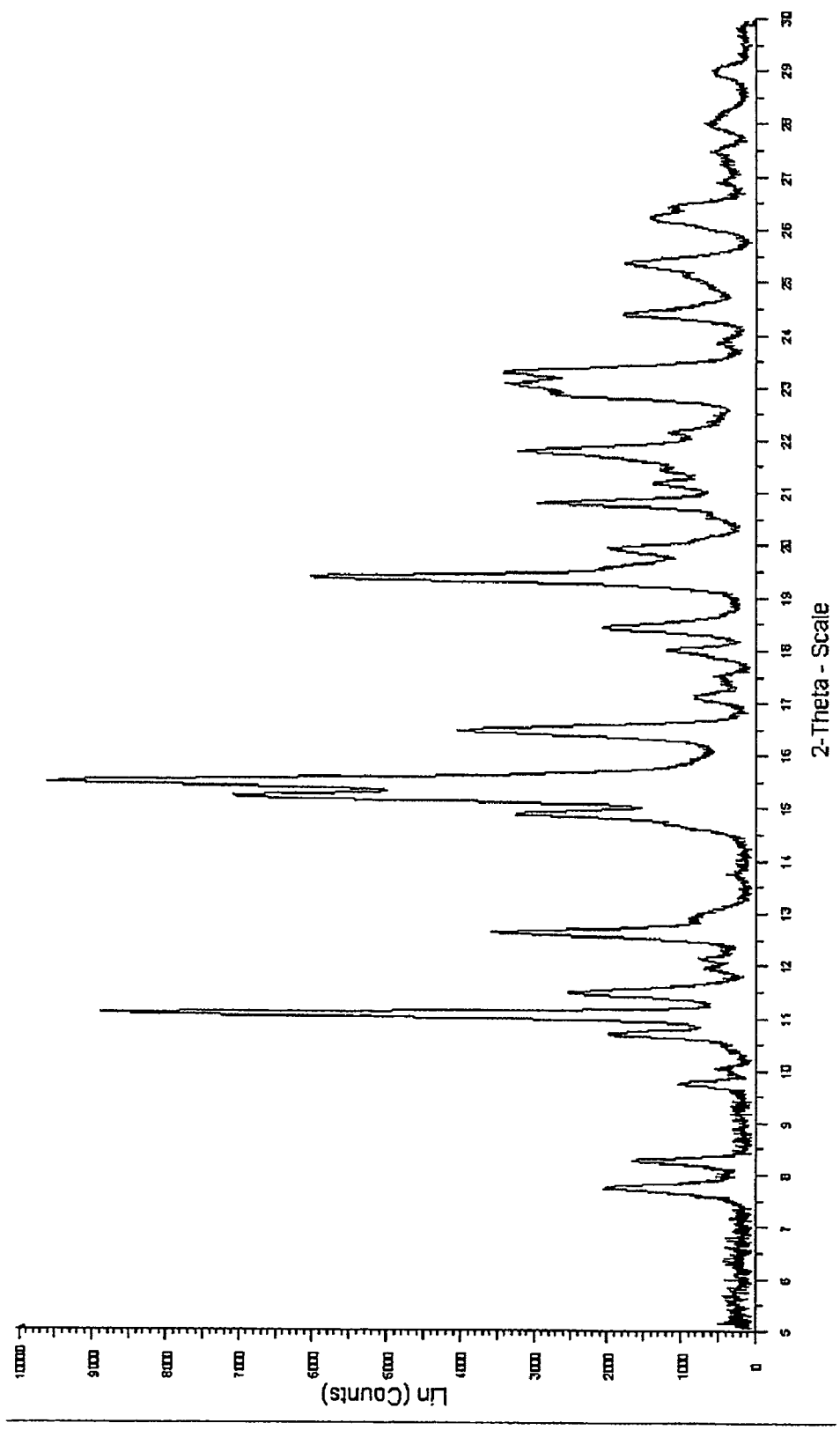
FIG. 21 depicts the X-ray powder diffraction pattern for the Acetonate of compound 2.

Compound 1 was dissolved in 32 volumes of acetone at elevated temperature. A stoichiometric amount of glucuronic acid, dissolved in 3-4 volume of water, was added at once. Nucleation started immediately. The resulting mixture was stirred on ice for 30 minutes then left overnight without stirring. The title compound was collected by filtration. FIG. 21 depicts the powder X-ray diffraction pattern of the Acetonate. The Acetonate of compound 2 converts to Form I upon drying.

Example 12

Integrations of signals from glucuronic acid were compared with the unique peak of compound 1 (FIG. 4) to obtain molar ratio of glucuronic acid to compound 1. The ratio of acid to 1 observed ranged from 0.94 to 0.95.

Comparative equilibrium solubilities of the hydrochloride, hydrobromide, and glucuronate salts of compound 1 are listed in Table 10.

TABLE 10

Comparative Equilibrium Solubilities of Salts of Compound 1

| Salt of compound 1 | Solubility (mg/mL) (freebase equivalent) | pH |
| --- | --- | --- |
| freebase (1) | 0.22 | 4.72 |
| hydrochloride | 1.46 | 4.82 |
| mesylate | 0.021 | 4.2 |
| hydrobromide | 1.26 | 4.73 |
| glucuronate (2) | 19.93 | 4.25 |

Example 12

Preparation of Extended Release Formulations

Formulation A

An extended release tablet formulation is prepared of compound 2 (30% w/w), microcrystalline cellulose (29% w/w), hypromellose (40% w/w), and magnesium stearate (1% w/w) by blending compound 2, a portion of the microcrystalline cellulose, hypromellose, and some magnesium stearate, and then dry granulating the mixture via roller compaction. The resulting compacts are then sized by milling and/or screening. The remaining microcrystalline cellulose is blended in and the granulation is lubricated with the remaining magnesium stearate and compressed into tablets.

Formulation B

Another example of an extended release dosage form is a multiparticulate formulation with a core comprised of compound 2 (70% w/w) and microcrystalline cellulose (30% w/w). The core is prepared by combining the components and granulating them with water in a planetary mixer. Then, using the Nica® System, the resulting wet mass is extruded through a 1.0 mm screen. The extrudates are then transferred to the spheronizer and spun at approximately 700 rpm until spherical pellets are obtained (2-3) minutes. The wet pellets are then dried in a fluid bed dryer to a moisture level of 2-5%. The dried pellets are passed through a 18 mesh screen to remove larger oversize pellets. The pellets are then coated with a seal coat comprised of Opadry® Clear (5% w/w) and water (95% w/w). This is performed by first fitting the fluid bed apparatus with a Wurster column and bottom spray nozzle system, then applying the Opadry® seal coat at an inlet temperature of approximately 60° C., a coating solution spray rate of 5-10 grams/min, atomization pressure of 1-2 bar. The desired product temperature is 38-43° C. After approximately a 2% weight gain of the seal coat is achieved, an ethylcellulose coat can be applied. This coat is comprised of Surelease® (aqueous ethylcellulose dispersion, 25% solids; 5% w/w) and water (95% w/w) and is applied in a similar fashion as the seal coat to a weight gain of 3-8%. After the ethylcellulose coat is applied, the pellets are dried for an additional 5-10 minutes. The pellets are then removed and screened through an 18-mesh screen to remove agglomerates and oversize particles.

We claim:
1. Compound 2:

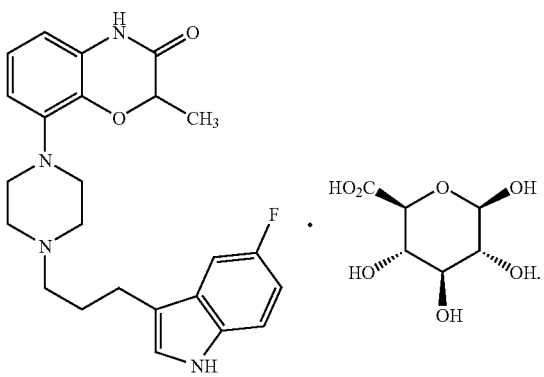

2. The compound according to claim 1, wherein said compound is in solid form.
3. The compound according to claim 2, wherein said compound is crystalline.
4. The compound according to claim 3, wherein said compound is a crystalline solid substantially free of amorphous compound 2.
5. The compound according to claim 1, wherein said compound is substantially free of impurities.
6. A method for preparing compound 2:

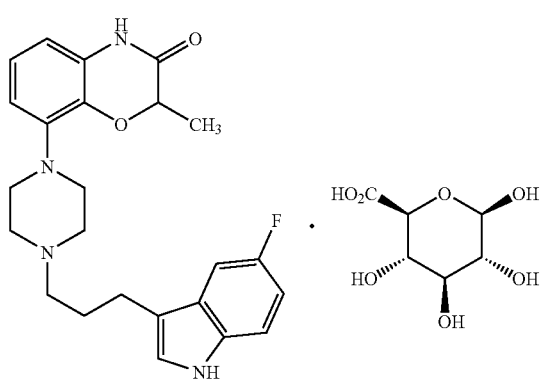

comprising the steps of:
providing compound 1:

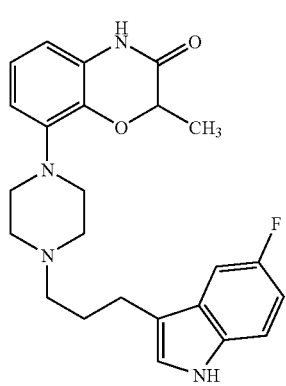

combining compound 1 with glucuronic acid in a suitable solvent; and
optionally isolating compound 2.
7. The method according to claim 6, wherein said suitable solvent is a protic solvent, a polar aprotic solvent, or a mixture thereof.
8. A method for preparing compound 2:

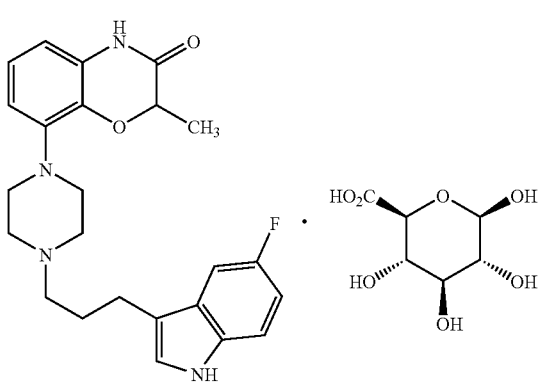

comprising the steps of:
combining compound 1:

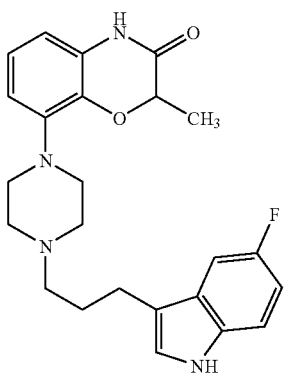

with a suitable solvent and heating to form a solution thereof;
adding glucuronic acid to said solution; and
optionally isolating compound 2.
9. A pharmaceutically acceptable composition comprising the compound according to claim 1, and a pharmaceutically acceptable carrier, adjuvant, or vehicle.
10. The composition according to claim 9, wherein said composition is an injectable formulation for intravascular delivery.
11. The composition according to claim 9, wherein said composition is an injectable formulation for intramuscular delivery.
12. A method of modulating one or more GPCRs in a biological sample, comprising contacting said biological sample with a compound according to claim 1.
13. A method of treating, or lessening the severity of, one or more disorders selected from Parkinson's disease, psychoses including schizophrenia, mania, psychotic depression, bipolar disorder, depression, stress/anxiety, Alzheimer's disease, Huntington's disease, panic disorder, obsessive compulsive disorder, an eating disorder, drug addiction, social phobias, aggression or agitation, migraine, scleroderma, Raynaud's phenomenon, emesis, a GI tract disorder related to the regulation of peristalsis, RLS, or prolactin secretion arising from tumours of the pituitary gland, wherein said method comprises administering to a patient a composition according to either of claims 9 or 10.

14. The method according to claim 13, wherein said disorder is Parkinson's disease.

15. The method according to claim 13, wherein said disorder is a psychosis selected from schizophrenia, mania, psychotic depression, and bipolar disorder.

16. The method according to claim 13, wherein said disorder is depression, stress/anxiety, panic disorder, obsessive compulsive disorder, an eating disorder, drug addiction, or a social phobia.

17. The method according to claim 13, wherein said disorder is aggression or agitation.

18. The method according to claim 13, wherein said disorder is Alzheimer's disease, Huntington's disease, migraine, scleroderma, Raynaud's phenomenon, emesis, a GI tract disorder related to the regulation of peristalsis, RLS, or prolactin secretion arising from tumours of the pituitary gland.

19. The crystalline compound according to claim 3, wherein said compound is Form I.

20. The crystalline compound according to claim 18, having one or more peaks in its powder X-ray diffraction pattern selected from those at about 17.5, 22.5, 19.9, 3.9, and 12.2 degrees 2-theta.

21. The crystalline compound according to claim 3, wherein said compound is Form II.

22. The crystalline compound according to claim 3, wherein said compound is a hydrate of compound 2.

23. The crystalline compound according to claim 22, wherein said hydrate is selected from Hydrate I or Hydrate II.

24. The crystalline compound according to claim 3, wherein said compound is a solvate of compound 2.

25. The crystalline compound according to claim 24, wherein said solvate is selected from the Methanolate, Ethanolate I, Ethanolate II, Isopropanolate I, Isopropanolate II, or the Acetonate.

\* \* \* \* \*